(12) United States Patent
Stobbe

(10) Patent No.: US 9,228,579 B2
(45) Date of Patent: Jan. 5, 2016

(54) METHOD AND DEVICE FOR INDUSTRIAL BIOLAYER CULTIVATION

(75) Inventor: Per Stobbe, Holte (DK)

(73) Assignee: Stobbe Tech A/S, Holte (DK)

( * ) Notice: Subject to any disclaimer, the term of this patent is extended or adjusted under 35 U.S.C. 154(b) by 939 days.

(21) Appl. No.: 13/125,399

(22) PCT Filed: Dec. 18, 2009

(86) PCT No.: PCT/DK2009/000259
§ 371 (c)(1),
(2), (4) Date: Apr. 21, 2011

(87) PCT Pub. No.: WO2010/069319
PCT Pub. Date: Jun. 24, 2010

(65) Prior Publication Data
US 2011/0263021 A1 Oct. 27, 2011

(30) Foreign Application Priority Data

Dec. 19, 2008 (DK) .............................. PA 2008 01815
Oct. 19, 2009 (DK) .............................. PA 2009 01131
Oct. 21, 2009 (DK) .............................. PA 2009 01142
Oct. 29, 2009 (DK) .............................. PA 2009 01165

(51) Int. Cl.
*C12M 1/34* (2006.01)
*C12M 3/04* (2006.01)
*F04B 43/00* (2006.01)
*C12M 1/00* (2006.01)
(Continued)

(52) U.S. Cl.
CPC ............ *F04B 43/0081* (2013.01); *C12M 23/34* (2013.01); *C12M 23/42* (2013.01); *C12M 25/14* (2013.01); *F04B 43/073* (2013.01); *F04B 43/0733* (2013.01); *F04B 43/0736* (2013.01)

(58) Field of Classification Search
CPC ....... C12M 27/02; C12M 35/04; C12M 21/04; C12M 29/10; C12M 23/34; C12M 23/42; C12M 25/14; F04B 43/0081; F04B 43/073; F04B 43/0733; F04B 43/0736
USPC .......... 435/243, 286.1, 287.1, 289.1, 398, 420
See application file for complete search history.

(56) References Cited

U.S. PATENT DOCUMENTS 4,201,845 A 5/1980 Feder et al.
4,514,499 A 4/1985 Noll
(Continued)

FOREIGN PATENT DOCUMENTS

EP 155237 A3 6/1986
EP 237666 A1 9/1987
(Continued)

OTHER PUBLICATIONS

Li et al.: "A single use, scalable perfusion bioreactor system" Bioprocess International/Supplement, Apr. 1, 2009, XP002586726 cited in the application figure 3.
(Continued)

*Primary Examiner* — Michael Hobbs
(74) *Attorney, Agent, or Firm* — Fish & Richardson P.C.

(57) ABSTRACT

A compact, high-yield, bio-reactor for use as small, medium and large-scale production unit for therapeutic proteins, proteins in general and enzymes based on controlled activity of the cells or micro organisms and the production of such as high value antibodies for pharmaceutical and/or bio-diagnostic applications.

16 Claims, 11 Drawing Sheets

Figure 1:
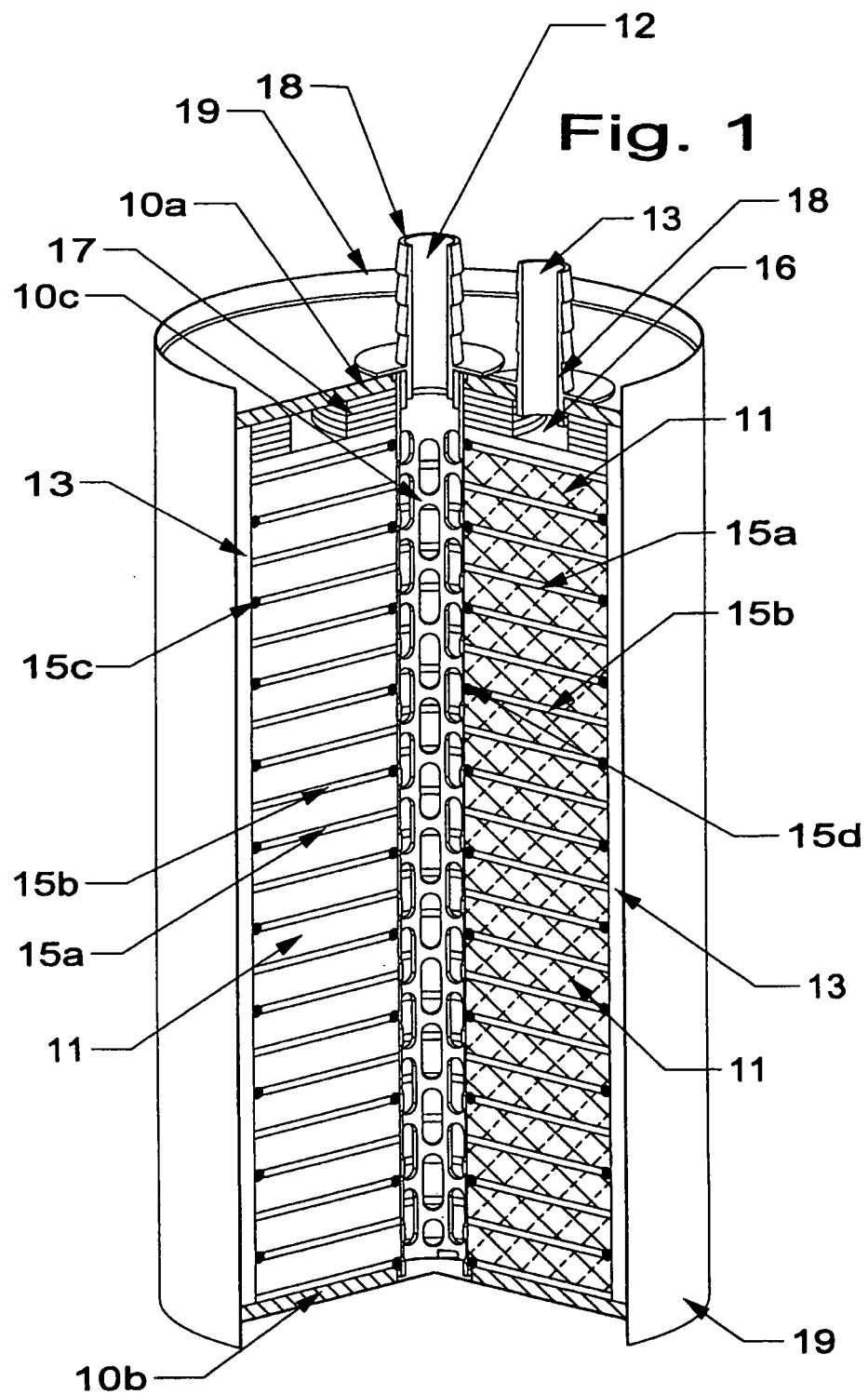

(51) Int. Cl.
*C12M 3/00* (2006.01)
*C12M 1/12* (2006.01)
*F04B 43/073* (2006.01)

(56) References Cited

U.S. PATENT DOCUMENTS

| | | | |
|---|---|---|---|
| 4,546,083 A | 10/1985 | Meyers et al. | |
| 4,789,634 A | 12/1988 | Muller et al. | |
| 4,937,196 A | 6/1990 | Wrasidlo et al. | |
| 4,948,728 A | 8/1990 | Stephanopoulos et al. | |
| 4,978,616 A | 12/1990 | Dean, Jr. et al. | |
| 5,190,878 A * | 3/1993 | Wilhelm | 435/297.2 |
| 5,266,476 A | 11/1993 | Sussman et al. | |
| 5,501,971 A | 3/1996 | Freedman et al. | |
| 5,543,047 A | 8/1996 | Stoyell et al. | |
| 5,563,069 A | 10/1996 | Yang | |
| 6,844,187 B1 | 1/2005 | Wechsler et al. | |
| 2006/0115894 A1 | 6/2006 | Wan | |
| 2008/0003676 A1 | 1/2008 | Sheridan et al. | |
| 2008/0131957 A1 | 6/2008 | Ryan et al. | |
| 2008/0175825 A1 * | 7/2008 | Hampson et al. | 424/93.7 |
| 2009/0176301 A1 | 7/2009 | Oldenburg et al. | |
| 2009/0311776 A1 | 12/2009 | Kelly, Jr. et al. | |
| 2010/0075405 A1 * | 3/2010 | Broadley et al. | 435/286.1 |

FOREIGN PATENT DOCUMENTS

| | | |
|---|---|---|
| WO | WO2005118771 A1 | 12/2005 |
| WO | WO2007039600 A1 | 4/2007 |
| WO | WO2007142664 A1 | 12/2007 |

OTHER PUBLICATIONS

Cell Culture Bioreactors, pp. 1-23 (Aug. 2011).
Cellular Bioprocess Technology (2004), University of Minnesota, pp. 18-24.
Duk Jae Oh et al., "High-Density Continuous Cultures of Hybridoma Cells in a Depth Filter Perfusion System", Biotechnology and Bioengineering, vol. 44, pp. 895-901 (1994).
Joon Chul Lee et al., "Recombinant Antibody Production by Perfusion Cultures of rCHO Cells in a Depth Filter Perfusion System," Biotechnol. Prog. (2005), 21, 134-139.
Tzyy-Wen Chiou et al., "A Fiber-Bed Bioreactor for Anchorage-Dependent Animal Cell Cultures: Part I. Bioreactor Design and Operations", Biotechnology and Bioengineering, vol. 37, pp. 755-761 (1991).
Sei Murakami et al., "A Fiber-Bed Bioreactor for Anchorage-Dependent Animal Cell Cultures: Part II. Scaleup Potential", Biotechnology and Bioengineering, vol. 37, pp. 762-769 (1991).
Guozheng Wang et al., "Modified CelliGen-packed bed bioreactors for hybridoma cell cultures", Cytotechnology 9:41-49 (1992).
Chen et al., "A Fibrous-bed bioreactor for continuous production of developmental endothelial locus-1 by osteosarcoma cells", Journal of Biotechnology (2002).
H. T. Lokhande et al., "Grafting onto polyester fibres", Colloid & Polymer Science, vol. 262, No. 2, pp. 127-130 (1984).
C. E. Turick et al., "Review of Nonconventional Bioreactor Technology", Idaho National Engineering Laboratory (1993).
Fassnacht et al., "Long-term cultivation of immortalised mouse hepatocytes in a high cell density, fixed-bed reactor", Biotechnology Techniques, vol. 12, No. 1, (Jan. 1998), pp. 25-30.
Meuwly et al., "Packed-bed bioreactors for mammalian cell culture: Bioprocess and biomedical applications", Biotechnology Advances 25 (2007) pp. 45-56.
Joon Chul Lee et al., "Recombinant Antibody Production by Perfusion Cultures of rCHO Cells in a Depth Filter Perfusion System", American Chemical Society and American Institute of Chemical Engineers, Published on Web Jan. 11, 2005.
Mark A. Applegate et al., "Development of a Single-Pass Ceramic Matrix Bioreactor for Large-Scale Mammalian Cell Culture", Biotechnology and Bioengineering, vol. 40, pp. 10-56-1068 (1992).

* cited by examiner

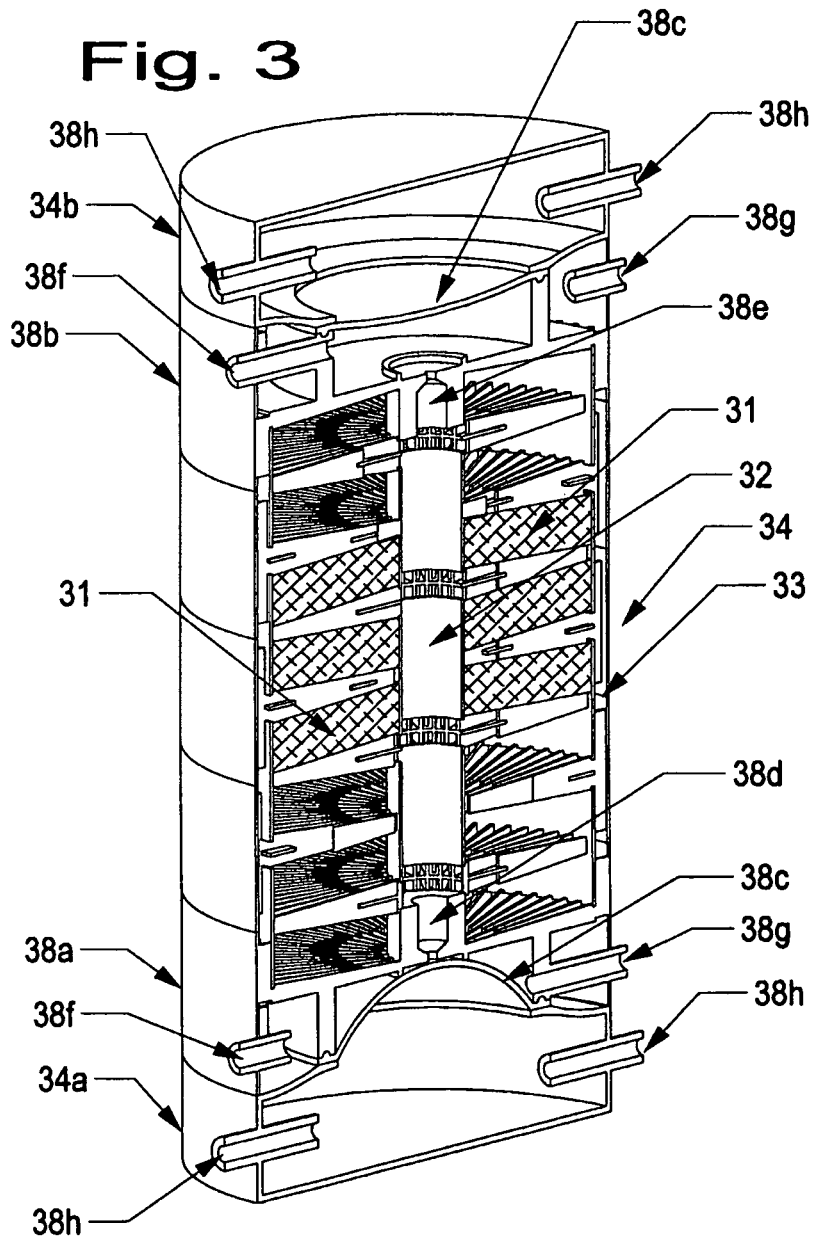

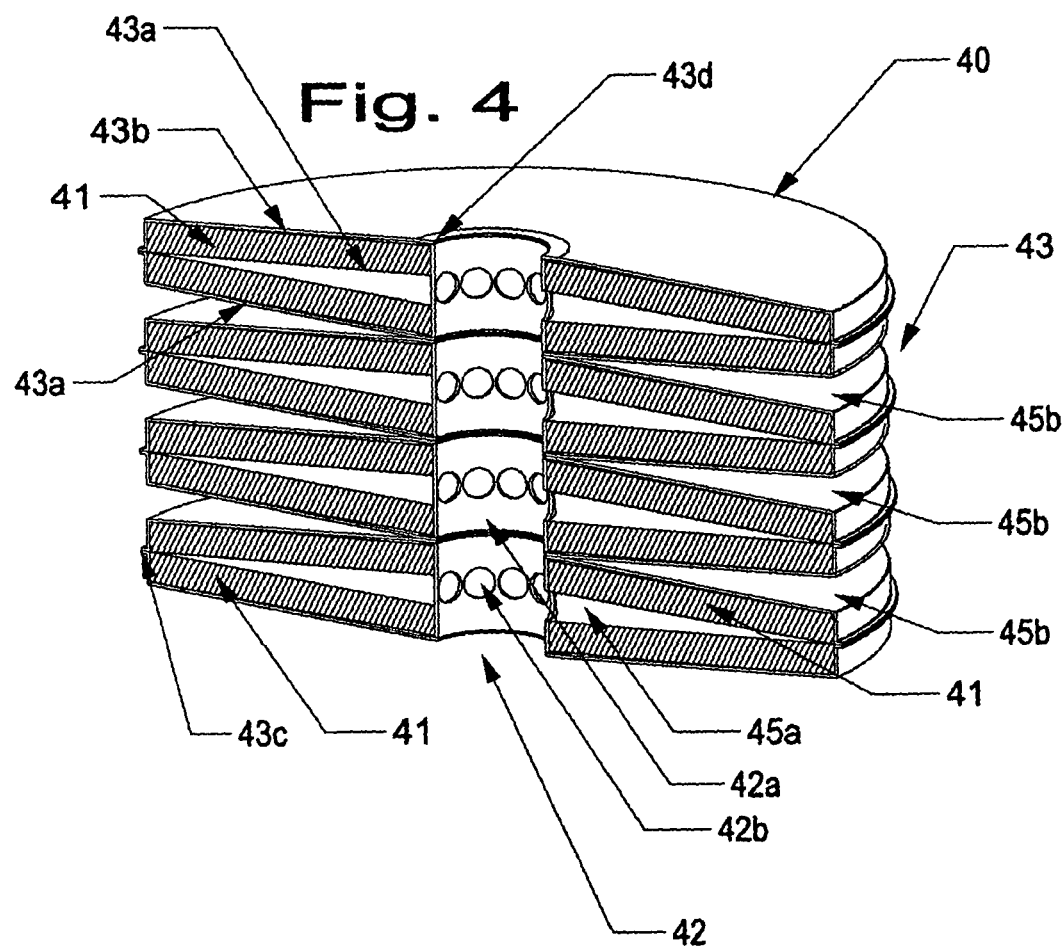

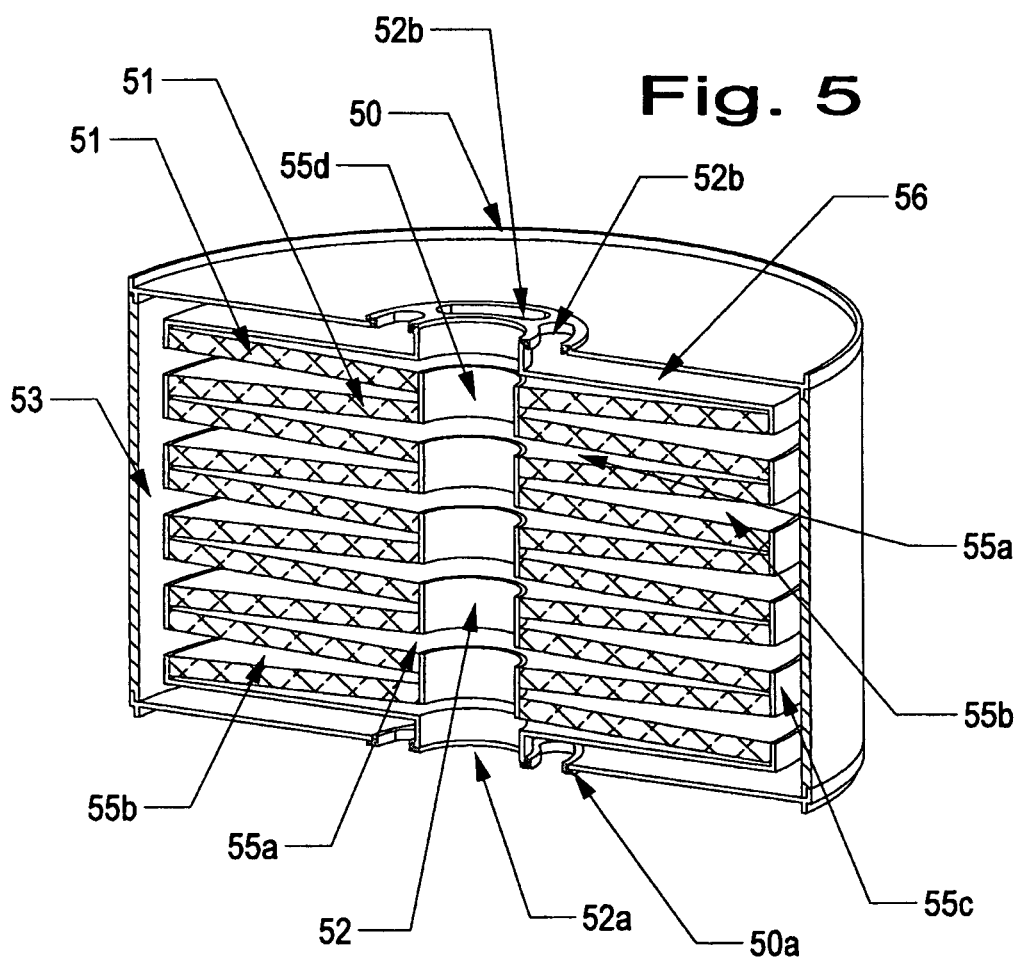

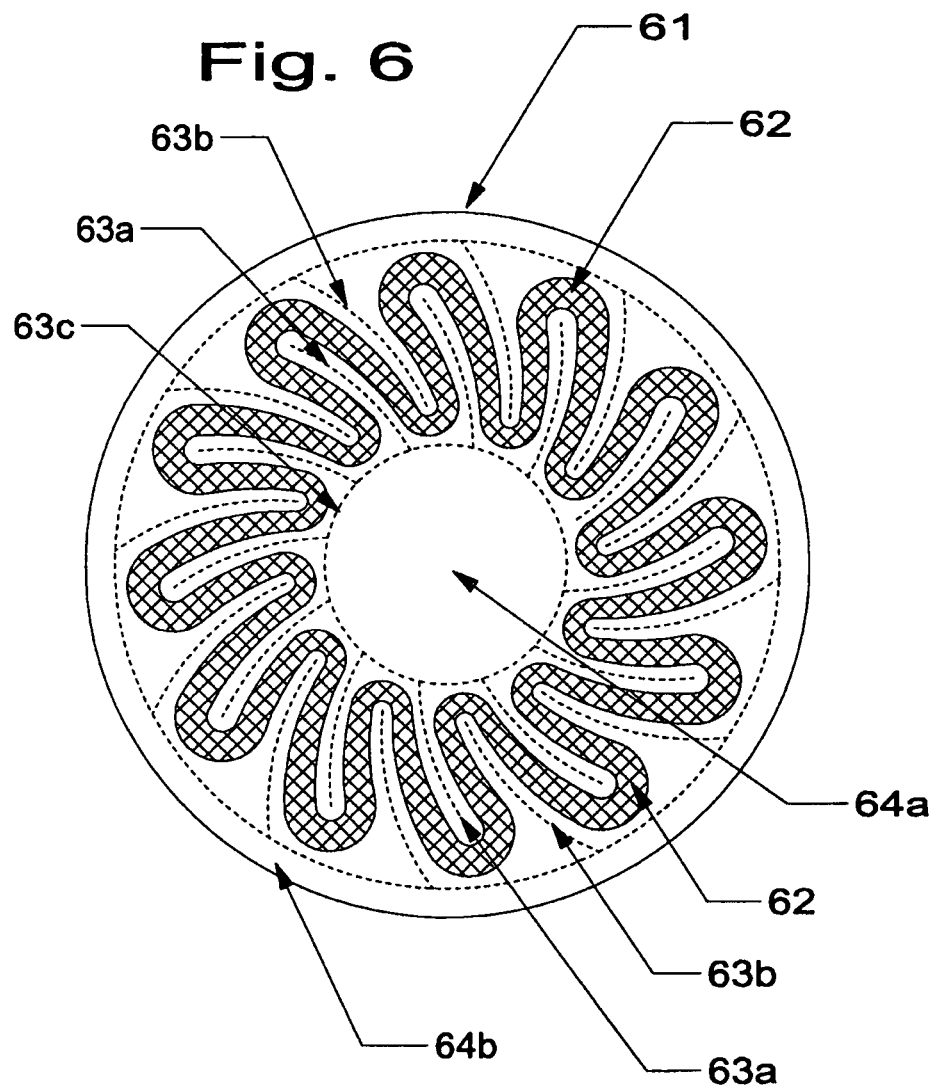

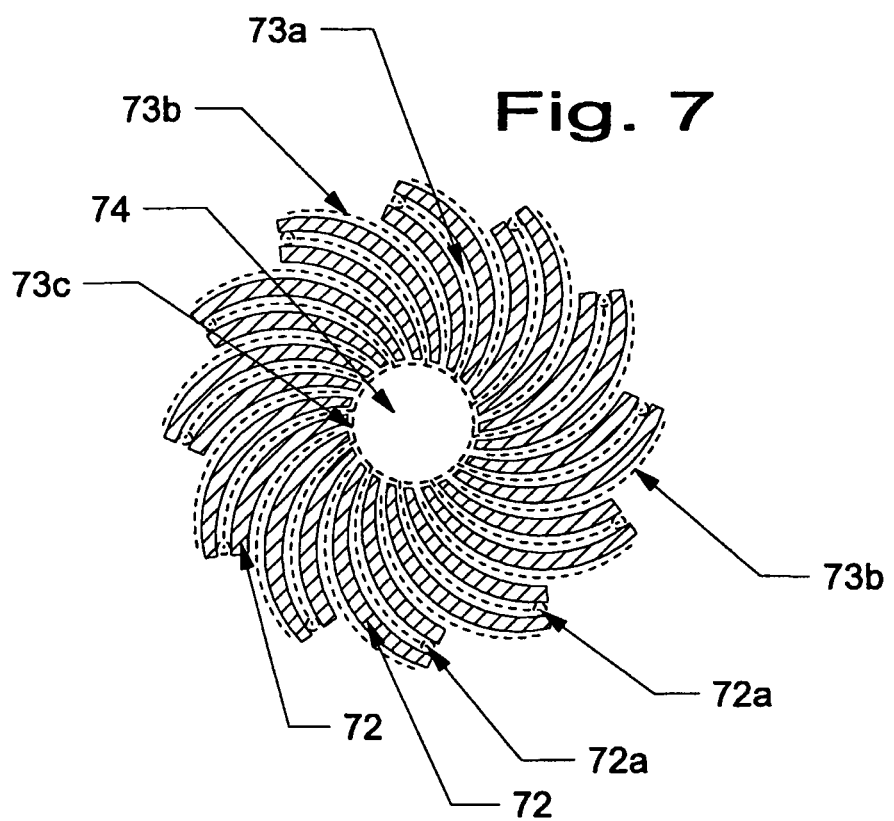

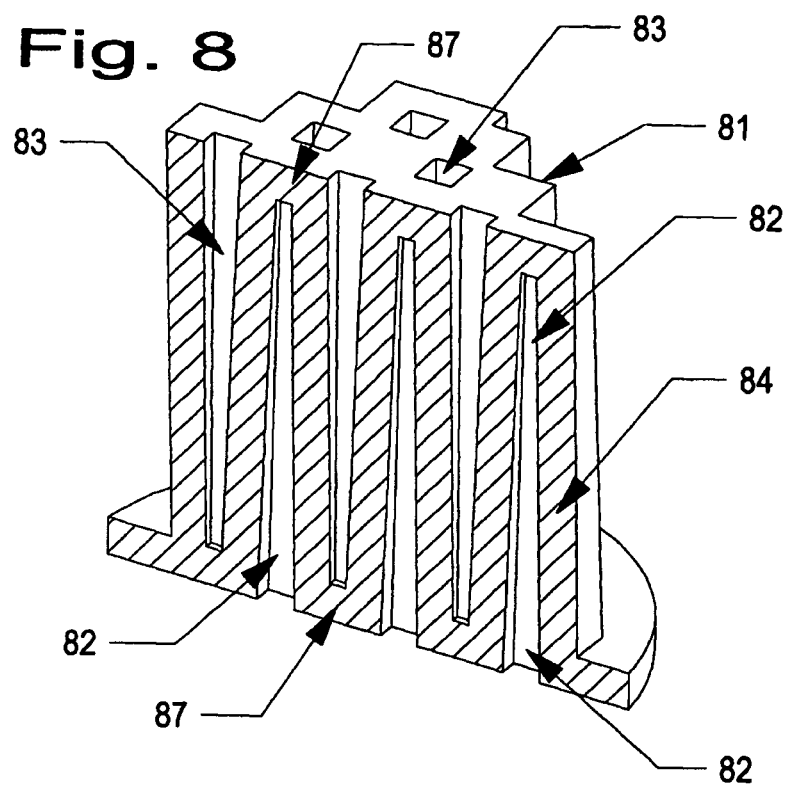
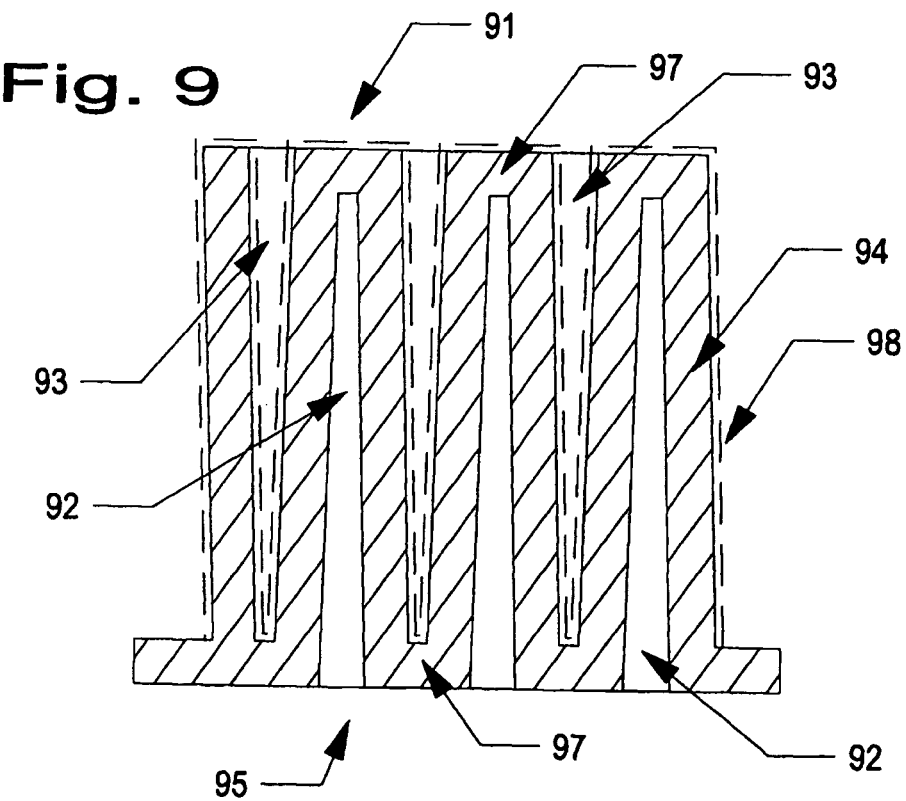

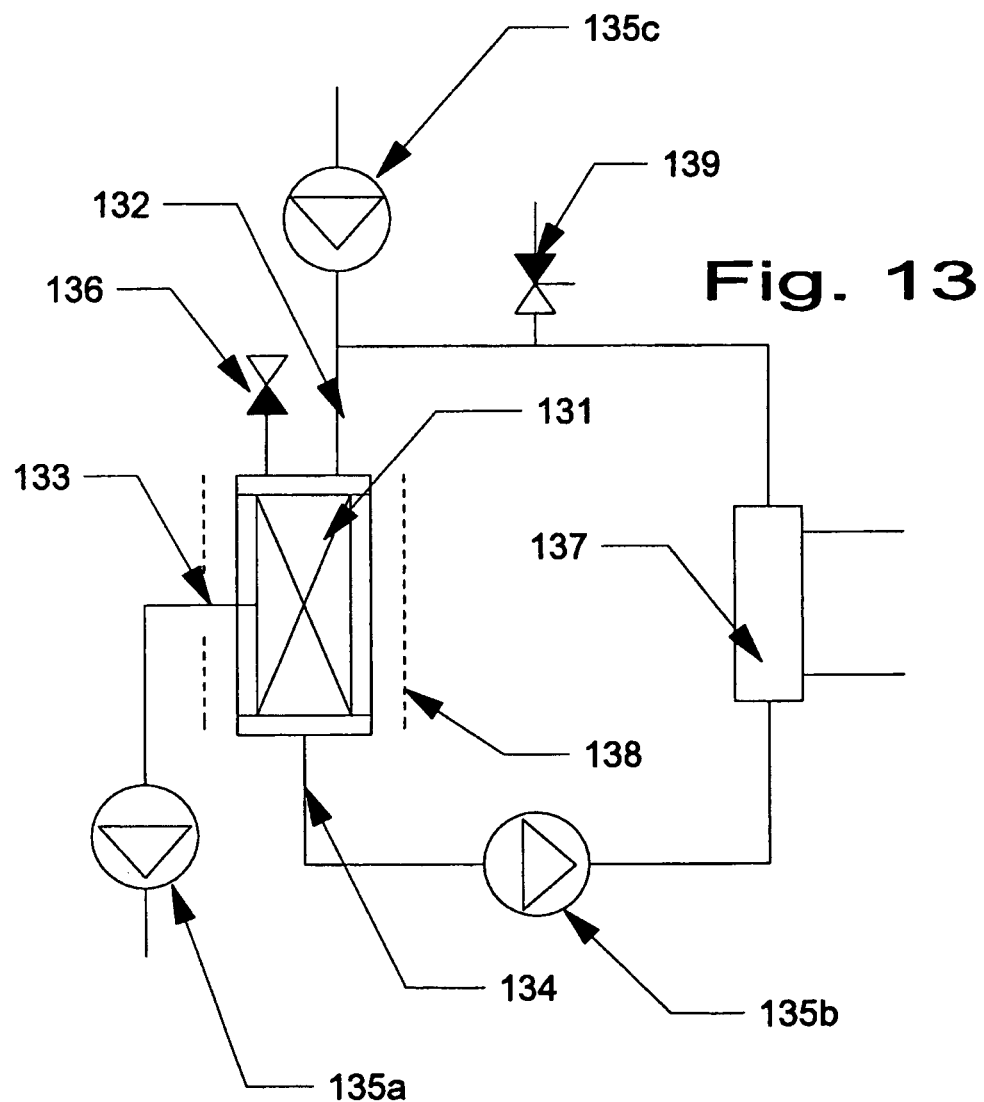

METHOD AND DEVICE FOR INDUSTRIAL BIOLAYER CULTIVATION

CROSS REFERENCE TO PRIOR APPLICATIONS

This is a U.S. National Phase application under 35 U.S.C. §371 of International Patent Application No. PCT/DK2009/000259, filed Dec. 18, 2009, and claims the priority of Danish Patent Application No. PA/2008/01815, filed Dec. 19, 2008; Danish Patent Application No. PA/2009/01131, filed Oct. 19, 2001; Danish Patent Application No. PA/2009/01142, filed Oct. 21, 2009; and Danish Patent Application No. PA/2009/01165, filed Oct. 29, 2009, all of which are incorporated by reference herein. The International Application published in English on Jun. 24, 2010 as WO 2010/069319 under PCT Article 21(2).

TECHNICAL FIELD

The present invention relates to device, such as a bio-reactor or a bio-reactor module, for producing a bio-material and/or a therapeutic material, a process for creating a micro-organism friendly environment for use in a bio-reactor and methods for operating said bio-reactor.

BACKGROUND OF THE INVENTION

In bio-reactor technology large-scale production of bio-active compounds, including bio-polymers, from bacterial micro organisms is currently performed in batch fermenters and requires product purification downstream. One of the major limitations of the batch fermentation technology is the large volume of the fermenter needed to accomplish this task on a mass-scale (in the order of millions of tons/year) and the high cost for installing and operating such fermenters.

As an example, most recombinant antibodies approved for human use are currently produced by large-scale cultivation of mammalian micro organisms (e.g. Chinese Hamster Ovary cells, or CHO cells). The process is expensive because of its limited capacity. The investment needed to establish a culture unit for mammalian cells is substantial (approximately 10 million Euro is required for an antibody production of 1 kg/year).

By 2002 approximately 64 different Monoclonal Antibodies (MAbs) had been approved by FDA (US Food and Drug Administration)—a figure expected to rise to 500 in less than 10 years. Many Mabs are already in clinical trials. The production capacity of MAbs was 4,000 kg in 2005 and the capacity is currently (2009) estimated to 10,000 kg. Most of this capacity is provided by stirred tanks having a capacity of around 1 mio. liters. This capacity may not even be sufficient for the production of the few, so far clinically validated therapeutic antibodies.

A projected demand of an expected capacity of 50,000 kg/year by 2020 will require at least 5 times the present, conventional stainless steel stirred tank capacity. It is clear that a World wide bio-tech industry will need to invest heavily in more production capacity in order to increase the current production capacity.

There is clearly a need for novel and innovative bio-reactor devices as well as for alternative methods for the production of bio-active compounds using such bio-reactor devices.

The market for bio-reactors can be divided into the following groups:
  Bench-top equipment market, 1-10 liter size
  Pilot-scale equipment market, 10-100 liter size
  Small-production equipment market, 100-1000 liter
  Large-production equipment market, >1000 liter Current fermenter technologies exhibit a relatively unattractive surface-to-volume ratios (stirred tanks≈1 $m^2$/40 liters and hollow fibres≈1 $m^2$/10 liters). Scaling up bio-reactors for use in the production of adherent micro organisms today relies exclusively on the possibility of increasing the surface area that is available for the adhesion of the micro organisms. This can be done e.g. by increase the size of the reactors. Classical micro organism culture lab ware ranges from 1 to 500 $cm^2$ per stationary flask. The surface area to volume ratio is the range of from 1,000 to 2,000 $cm^2$/liter for rotating flasks. Rotating wall vessel systems on the market would at best reach a ratio of 7.5 $m^2$ in a 2.5 $m^3$ volume.

Multi-plate systems, like OptiCell from Nunc, require large, thermo-controlled volumes to be efficient when used with a high surface area. To face these limitations, micro-carrier approaches, e.g. Cytodex from GE Healthcare) have been developed and such micro-carriers can bring the surface area up to approx. 9 $m^2$/liter for stirred suspension cultures where micro organisms are sensitive to shear forces due to stirring—thus covering only partially the available surface area with micro organisms.

Besides the limitation of the surface area available for micro organisms anchoring, additional problems exist, including cultivation difficulties, undesirable oxygen gradients, tension control, pH control and a general lack of homogeneity of nutrient delivery throughout the bio-reactor.

Micro organism expression levels depend upon the type of molecule to be produced, which range from approx. 5 mg/liter/day for laboratory clones to up to 1 g/liter/day under ideal industrial condition. Based on such production rates, the expected production achievable with a 20 liter continuous, wall-forced-flow bio-reactor is a daily, steady state production of up to 2 grams of bioactive compound per day. Due to expected benefits related to bio-reactor geometry, surface properties, flow control and distribution of nutrients, these production rates might be further improved. By comparison, a classical batch bio-reactor based on micro carriers and duration of 8-10 days may at best produce 10 mg per liter. Accordingly, a 20 liter bio-reactor would produce at the most 200 mg bioactive compound per batch.

Conventional Methods and System Designs

Bio-reactor design is a complex engineering task. Under optimum conditions, the micro organisms must be able to perform their desired function with a 100 percent rate of success. The bio-reactor's environmental conditions, like gas content (i.e., air, oxygen, nitrogen and carbon dioxide), flow rates, temperature, pH and agitation speed/circulation rate need to be closely monitored and controlled. In a traditional, batch bio-reactor the nutrient volume is constant—it is not exchanged and it is stirred throughout the duration of the fermentation.

In a Continuous Flow Stirred Tank bio-reactor (CSTR or chemostat), the continuous flow of fresh medium is fed into the bio-reactor at a constant rate, and medium is mixed with micro organisms and an undesirable mix of cells and product leaves the bio-reactor at the same rate. A fixed bio-reactor volume is maintained and ideally, the effluent stream should have the same composition as the bio-reactor contents. The culture is fed with fresh medium containing one and sometimes two growth-limiting nutrients, including e.g. glucose. The concentration of the micro organisms in the bio-reactor is controlled by the concentration of the growth limiting nutrient level. A steady state micro organism concentration is reached when the density of the micro organisms and the nutrient concentration are constant.

A bio-reactor is a suitable device for growing both anchorage dependent and suspended micro organism. Ideally, any micro organism culture bio-reactor must maintain a sterile culture of micro organisms under medium conditions which maximize micro organism growth and productivity. In the aerobic process, optimal oxygen transfer and access is perhaps the most difficult task to accomplish. Oxygen is poorly soluble in water at atmospheric pressure, even less in fermentation broths, usually helped by agitation, which is also needed to mix nutrients and to keep the fermentation homogeneous. There are, however, limits to the speed of agitation in stirred tank bio-reactors, due both to high power consumption and damages to the micro organism.

In bio-reactors where the goal is to cultivate micro organisms or tissue cells for experimental or therapeutic purposes, the design is often significantly different from industrial bio-reactors. Many micro organisms and tissues, especially mammalian ones, must have a surface or other structural support in order to grow, and agitated environments are often destructive to these micro organism types and tissues. Higher organisms also need more a complex growth medium composition. The most crucial step in the design of monolithic reactors is the proper distribution of nutrient fluids over the reactor cross section.

Flasks for laboratory use are made from either glass or polycarbonate and very commonly they are used only for small scale productions. The maximum surface available in a single flask is 500 $cm^2$ as offered from Thermo Fishers Danish department NuncBrand in the TripleFlask model. If stacked in a one meter high setup the flasks can offer a surface area of 0.6 $m^2$/20 liters volume into a manually handled process.

The German company Sartorious market CELLine cultivation flasks with a built-in micro organism separation method offering nutrient re-circulation and easier product harvesting. Flask surface areas range from 350 $cm^2$ to 1000 $cm^2$ for anchored micro organisms. Also available is a cassette based, stackable system for small, industrial micro organism cultivation on porous polymeric membranes. Each cassette offers 100 $cm^2$ area and 20 cassettes fit into a ready made cassette support system offering in total adhesion area of 2,000 $cm^2$. Each cassette has its own two resealing access ports which provide a closed, growth environment with a sterile fluid path. It is purely intended for anchorage-dependent cells.

Industrial vessel fermenters from Novaferm in Sweden or NNE (Novo Nordisk Engineering) in Denmark offer cultivation systems based on micro organisms suspended in the nutrient. The contact between nutrients and the micro organism are supported by mechanical stirrers and this is far from optimal.

Packed bed bio-reactors with small polyester fibre bodies, like the FibraCell product from New Brunswick Scientific in the United States, features an axial flow path along the porous bodies typically enclosed in a glass vessel. The FibraCell product is originally developed in the early 1990ties by Mr. Avinoam Kadouri from Yeda and Weizmann Institute of Science, Israel, but already in the 1980ties had exceptionally high yields, typically $10^8$ micro organisms/$cm^3$ of bed volume depending on selected micro organisms, been reported. The small bodies are less than 6 millimeter in diameter and the polyester fibre diameter is approx. 6 μm, bulk gravity 1 g/$cm^3$, and the available growth surface areas >1200 $cm^2$/g. The CelliGen 310 type of bio-reactor, also from New Brunswick Scientific—when packed with 500 gram Fibra Cell mini bodies (and in general for small scale industrial application with 14 liters volume)—offer 500 gram×1200 $cm^2$=25 $m^2$ surface area equivalent to 5 $m^2$/liter. The flow path is exclusively axial in the columns. Greater height is generally the solution when seeking to add more packing volume and this demands a greater volumetric flow in the axial direction and this in turn increases the risk of cell damage along the packed bed. Furthermore, the longer the bed the higher is the risk of experiencing an increased lack of nutrients and $CO^2$ content in the opposite end of the fluid inlet. As the nutrient flow now also becomes the exhaust fluid, the flow in the axial direction has a maximal limit. Cell densities of up to $1\times10^8$ and expression levels of approx. 0.5 g/mL have been reported from various sources. Artellis from Belgium has recently started to promote such a technology with small polyester fibre bodies packed in stackable envelopes.

Packed bed bio-reactors with porous micro beads, such as micro spheres provided by GE Healthcare or others, are in general very expensive. The beads are typically filled with macro pores and typical have a diameter of from 0.01 millimeter to up to 5 millimeter. They are manufactured from e.g. cellulose, polyethylene glass, gelatine, silicone rubber, silica, etc. Cell densities of up to $1\times10^8$ have been reported with the use of micro beards.

Membrane bio-reactors (MBR) are bio-reactors having a cross flow filtration unit which enables continuous processes with total micro organism retention within the reactor to be realized. Provided that high dilution rates can be applied and that inhibition processes are avoided, high biomass concentrations can be reached, thereby improving the volumetric productivity. These membrane bio-reactors have been successfully applied to various microbial bio conversions, such as alcohol fermentation, solvents, organic acid production, starters, and wastewater treatment. On the basis of the biological reaction characteristics and bibliographic results available, there are several bottlenecks associated with this methodology.

Hollow fibre bio-reactors systems use polymeric round hollow fibres bundles into a circular body with all the fibres passing axially through the core. The hollow fibres system can be used for anchorage dependent and suspension micro organisms. Typically the hollow fibre on the inside of the tube is provided with a membrane giving selective passage of molecules depending on their size. In most cases, an ultra filtration type of membrane is used. The molecular cut-off of the membrane differs according to applications, ranging from a few thousand to a hundred thousand Daltons. The ultra filtration membrane prevents free diffusion of secreted product molecules from passing through the membrane and allows them to accumulate in the extra capillary space to a high concentration. The culture media is pumped usually through the fibre lumen, and micro organism grow in the extra capillary space, or the shell side. Supply of low-molecular weight nutrient to the micro organisms and the removal of waste product occur by diffusive transport across the membrane between the lumen and the shell spaces. Although the use of micro filtration hollow fibre membranes for micro organism culture is infrequent, it does find application in various research uses for studying metabolism and for the cultivation of anchorage-dependent or highly aggregated micro organism for which a convective flow of medium through the extra capillary space to bathe micro organism in medium is desired. Scaling-up of a hollow fibre system eventually is limited by the ability to extend the axial length of the fibre without incoming oxygen transfer limitation, creating gradients. Also scaling up the cartridge diameter eventually runs into flow distribution problems among thousands of fibres. The relatively high surface area to volume ratio that hollow fibre bio-reactors provide (100 $cm^2$/mL or more) and the high flux rates of fibres from FiberCell Systems Inc. can allow micro organism to grow at 100 times the density found in flask culture ($10^{*8}$ vs. $10^{*6}$/mL in flask) and is in fact one of the only cell culture methods that permits micro organism cultures at densities that rival those found in vivo.

Honeycomb ceramic bio-reactor systems are typically in the form of a cylinder made of a porous ceramics with square channels passing through the ceramic cylindrical body in the longitudinal direction. Micro organisms are inoculated into the channels and either adheres to the surface or become entrapped into the pores of the ceramic body walls. Medium is passed through the channels to provide nutrient and to remove the metabolites. In the ceramic system, the side on which the micro organisms is adhered is exposed to a slow stream of permeate. The ceramic bio-reactor, to some extent, can be considered a variant of the hollow fibre system described herein above. As in the hollow fibre system, ceramic reactors are supported by medium perfusion loops. Micro organism culture medium is pumped through the longitudinal channels in the ceramic core from a medium reservoir in a circulating loop configuration. Fresh medium is fed into the system, and harvested bioactive compounds are removed to the medium reservoir. Unlike the hollow fibre system, there is no membrane separating the micro organisms and the bulk medium. Products are secreted directly into the bulk medium. Essentially, the ceramic bio-reactor (like the OptiCell) can be used to conveniently replace a large number of roller bottles. As in the hollow fibre systems, oxygen concentration gradient develops along the axial direction and poses a limitation to the length and/or the physical size of the ceramic reactor.

A laminar flow along a channel is often not sufficient to establish a contact between nutrients and a micro organism. Turbulence is not created along the channels having relatively smooth surfaces and the flow will generally be lower at the edges compared to the flow at the flat wall between the edges. Attempts to increase channel density only serves to increase this problem. The air-lift type of membrane bio-reactors do cause some turbulence, but the bubble sizes prevents the oxygen containing bubbles from coming into contact with the micro organisms in the corners. Also, it has been reported that the bubbles may damage the cells. As there is no force to create an interaction between the many channels the nutrients flow along, the channels are not fed equally. More channels in parallel will not affect the flow, the mass and the nutrient transfer to the cells. The liquid distribution results in the provision of heterogeneous sub-environments and a non-uniform protein production. This in turn seriously limits the applicability and the commercial potential for using ceramic monoliths having square cells as bio-reactor supports for the cultivation of micro organisms in large scale fermentations.

Plastic bags, disposable bags are becoming the biggest seller today below 1,000 liter bio-reactor volume. Bags with media inside only need a mechanism inside the bag in order to constantly mix the nutrient with the suspended micro organism. Many different techniques are on the market based on rotating devices with direct mechanical or magnetic force transfer or waving actions. However, the mixer typically adds shear forces to the media and this may potentially damage the micro organisms. Micro carriers could also be used with the bag operation in a perfusion system without a mixer relying on external, positive displacement pumps.

Wave-bag is a single-use system which rock, wave a volume of nutrient in a flat plastic bag on a tray which is kept in simple motion by an external mechanical force. Typical max cell densities are in the range of from $1\text{-}2\times10^7$/mL when operating in perfusion mode.

U.S. Pat. No. 4,948,728 (G. Stephanopoules) discloses a porous, ceramic material with a plurality of flow passages and a biofilm in contact with an inner wall in a channel and a gas permeable membrane covering an outer wall. A separate oxygen flow along the outer wall permeates the membrane and ceramic housing to reach the biomaterial. Nutrients flow along the inner wall in direct contact with the biofilm. The basic idea behind the invention is to apply oxygen on one side and nutrient flow on the other side of a porous wall. The monoliths, as supplied in the late 1980ties from Corning, are all flow through monoliths originally intended for automobile catalyst support and described in the patent as having a cell density of either 200 cells/in$^2$ (cpsi) (column 10) or 300 (column 5) cells/in$^2$ (cpsi). The Cordierite ceramic monoliths used are characterised as having a pore size of less than 15 µm. The expression "race track" monoliths which is used in the specification indicates that the catalyst carriers originate from the automobile industry and have very thin walls—typically less than 0.5 millimeter. A maximum cell density—with every second channel blocked and designed for DPF (diesel particulate filter) use—would be 90 cells per square inch (cpsi). The use of a parallel wall DPF is not described in the US patent or any associated literature. In the '728 patent, FIG. 1 illustrates a flow through the monolith. FIG. 4 shows the oxygen appearance on one side of the porous wall and the nutrient appearance on the other side of the porous wall. FIG. 5 illustrates that the penetration of oxygen into the porous ceramic wall is not complete, but only partial. Accordingly, there is no forced, hydraulic nutrient or oxygen flow through the wall through which e.g. glucose and oxygen is supposed to flow. This means that the predominant amount of bio film does not receive oxygen and this in turn results in a reduced production capacity. FIG. 5 also shows that the bio film penetration is limited by the hydrophobic membrane and this results in reducing the total amount of micro organisms inside the matrix. The '728 patent does not disclose e.g. how the channel flow should be adapted and/or controlled, if the channels should be blocked for flow control, or how the separation of inlet/outlet channels should be arranged.

Later documentation from G. Stephanopoules shows that controlling the two different fluid flows is not solved via channel blocking, but can be solved via the introduction of multiple, porous ultra small diameter silicon rubber hoses one of which is placed in each channel in order to supply the oxygen. However, this is very impractical and more or less impossible on a ceramic body with 200 or 300 cells/in$^2$, where each channel width is only 1 millimeter or less.

Also, the '728 patent does not disclose any membrane separating the inlet from the outlet. Such a membrane would be required in order to prevent cells from passing through the bio-reactor and be expelled in the flow after the reactor. Also, a high pressure drop membrane playing an important factor in distribution of oxygen and nutrients is not mentioned at all.

Figure 11:
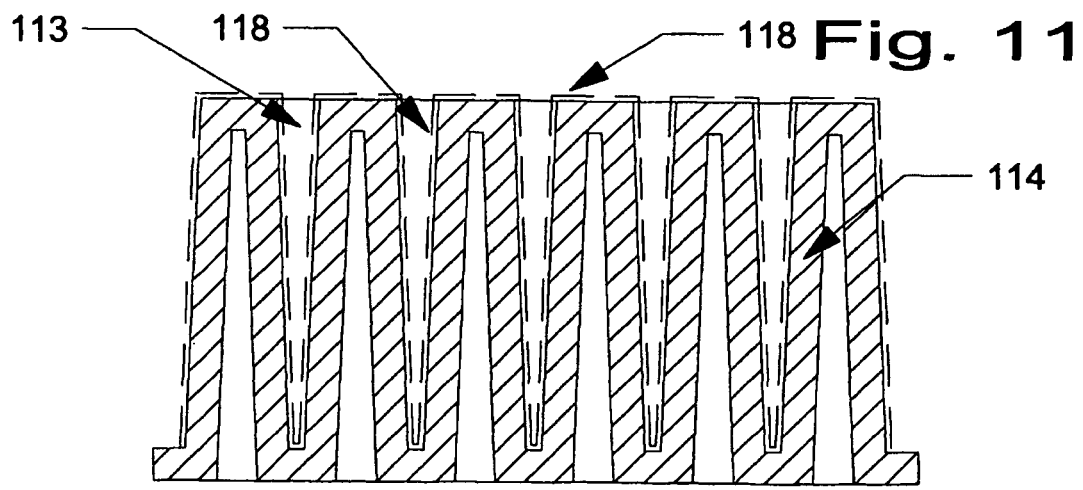

Reference is also made to the article by M. A. Applegate and G. Stephanopoulos, "Development of a Single-Pass Ceramic Matrix Bio-reactor for Large-Scale Mammalian Cell Culture," *Biotech methodology and Bio engineering*, volume 40, 1992, pp. 1,056-1,068. The use of porous hoses by Applegate and Stephanopoulos in each channel in order to supply oxygen (separate oxygenation system) is also described in the article "Review of Nonconventional Bio-reactor Technology" by C. E. Turick published 1993 by U.S. Department of Energy. On page 13, the cited equation refers to open channel ceramic bodies. FIG. 11 on page 12 illustrates one porous silicon tube in each channel in order to supply air/oxygen. It is obvious that channel closing has not been part of the patented invention. One other drawback of using Cordierite is the well known fact that a considerable amount of the pores as described by the porosity figure are so called closed pores. In other words there is no access to as much as 25% of the pores as they are not interconnected to other pores. The product reached a commercial status and became known as the OptiCell product in the industry.

U.S. Pat. No. 4,514,499 (Corning, Inc) describes a monolithic support for cell growth with the same general problems as describes above for U.S. Pat. No. 4,948,728.

U.S. Pat. No. 4,937,196 (New Brunswick Scientific) introduces the terms "membrane" and "micro porous membrane". A micro porous membrane does NOT allow the cells to pass the membrane. It is disclosed that "the dimension of the system is such that every cell is within 200 μm, preferably within 100 μm, of the oxygen source, i.e., the surface of an oxygen transport membrane". The oxygen supply is separated from the nutrient supply (which is void of oxygen) as the two individual feed spacers are separated by the membrane containing the cells. The laminated set-up disclosed in the '196 patent imposes the physical limit that the membrane containing the cells can have a maximum thickness of about 200 μm—as the oxygen supplying spacer is present only on one side of the cell supporting membrane.

Furthermore, it is described that the membranes are positive and do not allow the cells to pass the membrane. FIG. 9 illustrates the fluid path along the spacers from one end to the other, but no dual path feed spacer system capable of supporting such a teaching is disclosed. Nowhere does the '196 patent disclose how the individual feed spacers are anchored to the central tube in the spiral filter. Also, the legend to FIG. 10 indicate that a significant and undesirable pressure gradient is present, but the legend does not offer any suggestion as to how to avoid this.

U.S. Pat. No. 5,501,971 (New Brunswick Scientific) describes the Celligen system in the form of a packed bed of FibraCell polyester fibre based, flat carriers. The system currently on the market from New Brunswick Scientific demonstrates that cells adhere well to a polyester fibre, but the Celligen system is heavily limited by the thickness of the bed. As an increased bed thickness introduces or increases undesirable gradients in the bio-reactor, the bio-reactor device is not scalable and can be used for fermentations on a bench-top scale only.

U.S. Pat. No. 5,266,476 (Yeda) discloses a matrix of a thickness of from 50 to 500 μm and a surface area of 1 millimeter$^2$. The matrix is based on a polyester fibre and is in the form of a very small carrier know in the industry under the trade name FibraCell (supplied by both NBS and Bibby Sterilin Ltd, UK). FibraCell is a mini body approx. 6 millimeter in diameter and 0.6 millimeter thick. FibraCell has been used for various applications, among others by NBS (New Brunswick Scientific, USA) for manufacturing the Celligen product in which Fibra Cell bodies are randomly and efficiently packed in volumes of up to 1 liter. Larger reactor volumes are not possible due to gradient problems.

U.S. Pat. No. 4,546,083 (Stoll Corp) discloses a cylindrical device with fibres positioned around a tubular inlet—a spindle. The volume for the fibre matrix between the spindle and the cartridge inner wall are filled with fibres only.

U.S. Pat. No. 5,543,047 (Pall, Inc) describes a special pleating method improving among others also the potential area/volume ration and as described for filtration purposes only.

U.S. Pat. No. 5,563,069 (Ohio State University) is concerned with a packed bed structure based on cotton cloth in sheet shape.

WO2007/142664 (AMProtein Corp) discloses a method for increasing dissolved oxygen in a culture medium for a semi suspension culture of mammalian cells in a vessel. The vessel concept exploits constant height and varies the diameter in order to vary the fermenter volume in order to handle the gradient issue.

WO2007/039600 (Artelis) discloses a complicated flow pattern vessel device, which has an integrated mixer operating as circulation pump. The device is not suitable for up-scaling due to an undesirable increase in nutrient and/or oxygen gradients. Media re-circulation is performed by a mixer device internally in the vessel and this feature also seriously limits the prospects for up-scaling. Only perfusion mode operation is described. Gradients occurring in the central inlet zone results in the generation of an un-even cell density in the modules. The invention is based on packed micro porous micro carriers present inside modules, envelopes for cell support and/or empty modules suitable for the suspension of cells. Each radial fluid inlet between two envelopes supply media to only one of two envelopes. As described, most of the cells are not circulated, but those which are will be subjected to strong shear forces generated by the mixer impeller. Such cells are at risk of being seriously damaged. The described mixer physics exploit very limited pressure difference capabilities, both limiting the scale-up of the concept and increase shear forces in the fluid significantly.

U.S. Pat. No. 4,789,634 (KG Biologische Laboratorien) discloses a circular devise used for containing polymer microspheres, such as beads. The beads are located in round, stackable sieve boxes to ensure both a radial and an axial flow path.

The journal "BioProcess International" published in June of 2009 carries an article wherein AMprotein (China) states that they use large, randomly oriented, loosely packed cellulose fibre bodies, or Rasching alike soft elements, as "macro"-carriers for bio-reactor fermentations. It appears that the "Current" bio-reactor packed bed height is constant at approx. 150 millimeter and that the volume is modified by using 3 different diameters according to a reactor size ranging from 5 liters over 50 liters to 150 liters, thereby avoiding the problem of how to solve the problem of gradient formation.

MembroFerm is a product which was marketed by MBR Bio Reactor AG (Switzerland) in the early 1990ties. The product is in the form of a flat membrane bio-reactor separated by a thin film fluorocarbon matrix having a thickness of 0.6 millimeter.

None of the above-cited prior art references have solved the gradient problems associated with "packed bed" bio-reactor fermentations. Also, none of the above-cited prior art references have solved the problem of how to effectively scale a fermentation from a bench-top level to industrial production scale without the concomitant generation of undesirable gradients in a bio-reactor.

DESCRIPTION OF THE INVENTION

The present invention solves the problem of how to effectively scale a fermentation from a bench-top fermenter production level to an industrial scale production without the generation of undesirable gradients in an industrial scale bio-reactor.

The present invention also solves the problem of how to increase biological cell densities while at the same time reducing the volume of the bio-reactor in which the cells are fermented. This increased "compactness" of the bio-reactors according to the present invention reduces the cost of manufacturing production facilities needed for industrial scale bio-fermentations.

Accordingly, the present invention in a first aspect provides a gradient free, bio-reactor device and methods of efficiently cultivating live biological cells, such as e.g. micro organisms. According to the methods of the present invention, bio-molecules such as e.g. proteins, such as recombinant proteins, for example enzymes, antibodies, antibiotics and secondary metabolites can be more efficiently produced.

The biological cells become anchored to surfaces and fibres forming permeable stocks, such as essentially spherical discs of a predetermined thickness, wherein said stocks or discs comprise a porous matrix. The porous matrix comprises a plurality of inter-connected, open cells or pores and essentially no closed cells—i.e., essentially no cells not in liquid or fluid contact with an open cell or pore. The size of the open cells or pores of the matrix allows biological cells to adhere to the matrix material and habitate the internal volume—i.e. the matrix—of the stocks or discs. Biological cells can also adhere to matrix material on the outside—i.e. surface area—of the stocks or discs.

Due to a high surface area/disc volume ratio, fermentation of a density of biological cells can be supported. Due to i) bio-reactor design and ii) the physical nature of the matrix of the employed discs, the biological cells do not experience undesirable gradients in e.g. nutrients and oxygen and the vast majority of cells are supplied with sufficient nutrients and oxygen. Bio-reactors and methods of the present invention are designed so as to ensure an efficient culturing of biological cells, such as micro organisms, by allowing a feeding liquid comprising nutrients to obtain an essentially gradient free contact with biological cells adhered to bio-compatible surfaces and matrices of e.g. permeable discs.

The permeable disc of the present invention preferably does not contain or comprise a monolith, such as a ceramic thin wall, multi channel, and parallel channel monolith. Also, the permeable disc of the present invention preferably does not contain or comprise microspheres, such as e.g. essentially spherical beads.

The discs according to the present invention can be of any form and shape. In one embodiment the discs are circular with an optionally cut-out central portion to allow for the adaptation of a feeding tube or a collection reservoir in operable contact with the discs. The height (i.e. thickness) of the discs is preferably less than 500 millimeters, such as preferably less than 400 millimeters, for example preferably less than 350 millimeters, such as preferably less than 300 millimeters, for example preferably less than 250 millimeters, such as preferably less than 200 millimeters, for example preferably less than 150 millimeters, and preferably more than 1 millimeter, such as more than 2 millimeters, for example more than 5 millimeters, such as preferably more than 8 millimeters, for example preferably more than 10 millimeters, such as preferably more than 12 millimeters, for example preferably more than 14 millimeters, such as preferably more than 16 millimeters, for example preferably more than 18 millimeters, such as preferably more than 20 millimeters, for example preferably more than 22 millimeters, such as preferably more than 24 millimeters, for example preferably more than 26 millimeters, such as preferably more than 28 millimeters, for example preferably more than 30 millimeters, such as preferably more than 40 millimeters, for example preferably more than 50 millimeters.

The diameter of the discs (including the optionally cut-out central portion) will depend on the reactor design, including the height of the discs, and the disc diameter is, in one embodiment, preferably less than 500 centimeters, such as less than 480 centimeters, for example less than 460 centimeters, such as less than 440 centimeters, for example less than 420 centimeters, such as less than 400 centimeters, for example less than 380 centimeters, such as less than 360 centimeters, for example less than 340 centimeters, such as less than 320 centimeters, for example less than 300 centimeters, such as less than 280 centimeters, for example less than 260 centimeters, such as less than 240 centimeters, for example less than 220 centimeters, such as less than 200 centimeters, for example less than 190 centimeters, such as less than 180 centimeters, for example less than 170 centimeters, such as less than 160 centimeters, for example less than 150 centimeters, such as less than 140 centimeters, for example less than 130 centimeters, such as less than 120 centimeters, for example less than 110 centimeters, such as less than 100 centimeters, for example less than 90 centimeters, such as less than 85 centimeters, for example less than 80 centimeters, such as less than 75 centimeters, for example less than 70 centimeters, such as less than 65 centimeters, for example less than 60 centimeters, such as less than 55 centimeters, for example less than 50 centimeters, such as less than 45 centimeters, for example less than 40 centimeters, such as less than 35 centimeters, for example less than 30 centimeters, such as less than 25 centimeters, for example less than 20 centimeters, and preferably more than 1 centimeter, such as more than 2 centimeters, for example more than 3 centimeters, such as more than 4 centimeters, for example more than 5 centimeters, such as more than 6 centimeters, for example more than 7 centimeters, such as more than 8 centimeters, for example more than 9 centimeters, such as more than 10 centimeters, for example more than 12 centimeters, such as more than 14 centimeters, for example more than 16 centimeters, such as more than 18 centimeters.

The permeable disc fibres preferably has, in one embodiment, an average diameter in the range of from 0.01 micrometer to preferably less than 100 micrometers, such as an average fibre diameter of from 0.05 to preferably less than 100 micrometers, for example an average fibre diameter of from 0.10 to preferably less than 100 micrometers, such as an average fibre diameter of from 0.15 to preferably less than 100 micrometers, for example an average fibre diameter of from 0.20 to preferably less than 100 micrometers, such as an average fibre diameter of from 0.25 to preferably less than 100 micrometers, for example an average fibre diameter of from 0.50 to preferably less than 100 micrometers, such as an average fibre diameter of from 1.0 to preferably less than 100 micrometers, for example an average fibre diameter of from 2.0 to preferably less than 100 micrometers, such as an average fibre diameter of from 4.0 to preferably less than 100 micrometers, for example an average fibre diameter of from 6.0 to preferably less than 100 micrometers, such as an average fibre diameter of from 8.0 to preferably less than 100 micrometers, for example an average fibre diameter of from 10 to preferably less than 100 micrometers, such as an average fibre diameter of from 12 to preferably less than 100 micrometers, for example an average fibre diameter of from 14 to preferably less than 100 micrometers, such as an average fibre diameter of from 20 to preferably less than 100 micrometers, for example an average fibre diameter of from 25 to preferably less than 100 micrometers.

The packing density of the permeable disc fibres is preferably, in one embodiment, in the range of from 100 to 5000 gram/meter$^2$, such as from 100 to 200 gram/meter$^2$, for example from 200 to 300 gram/meter$^2$, such as from 300 to 400 gram/meter$^2$, for example from 400 to 500 gram/meter$^2$, such as from 500 to 600 gram/meter$^2$, for example from 600 to 700 gram/meter$^2$, such as from 700 to 800 gram/meter$^2$, for example from 800 to 900 gram/meter$^2$, such as from 900 to 1000 gram/meter$^2$, for example from 1000 to 1100 gram/meter$^2$, such as from 1100 to 1200 gram/meter$^2$, for example from 1200 to 1300 gram/meter$^2$, such as from 1400 to 1500 gram/meter$^2$, for example from 1500 to 1600 gram/meter$^2$, such as from 1700 to 1800 gram/meter$^2$, for example from 1800 to 1900 gram/meter$^2$, such as from 1900 to 2000 gram/meter$^2$, for example from 2000 to 2100 gram/meter$^2$, such as from 2100 to 2200 gram/meter$^2$, for example from 2200 to 2300 gram/meter$^2$, such as from 2300 to 2400 gram/meter$^2$, for example from 2400 to 2500 gram/meter$^2$, such as from 2500 to 2600 gram/meter$^2$, for example from 2600 to 2700 gram/meter$^2$, such as from 2700 to 2800 gram/meter$^2$, for example from 2800 to 2900 gram/meter$^2$, such as from 2900 to 3000 gram/meter$^2$, for example from 3000 to 3100 gram/meter$^2$, such as from 3100 to 3200 gram/meter$^2$, for example from 3200 to 3300 gram/meter$^2$, such as from 3300 to 3400 gram/meter$^2$, for example from 3400 to 3500 gram/meter$^2$, such as from 3500 to 3600 gram/meter$^2$, for example from 3600 to 3700 gram/meter$^2$, such as from 3700 to 3800 gram/meter$^2$, for example from 3800 to 3900 gram/meter$^2$, such as from 3900 to 4000 gram/meter$^2$, for example from 4000 to 4100 gram/meter$^2$, such as from 4100 to 4200 gram/meter$^2$, for example from 4200 to 4300 gram/meter$^2$, such as from 4300 to 4400 gram/meter$^2$, for example from 4400 to 4500 gram/meter$^2$, such as from 4500 to 4600 gram/meter$^2$, for example from 4600 to 4700 gram/meter$^2$, such as from 4700 to 4800 gram/meter$^2$, for example from 4800 to 4900 gram/meter$^2$, such as from 4900 to 5000 gram/meter$^2$, including any contiguous combination of the afore-mentioned sub-intervals.

Preferably, the volume of the open cells/pores of the matrix of the permeable discs/stacks is preferably less than 95% of the volume of the disc/stack itself, such as preferably less than 90%, for example less than 85%, such as less than 80%, for example less than 75%, such as less than 70%, for example less than 65%, such as less than 60%, for example less than 55%, such as less than 50%, for example less than 45%, such as less than 40%, for example less than 35%, such as less than 30%, for example less than 25%, such as less than 20%, and preferably more than 5%, for example more than 10%, such as more than 15% of the volume of the disc/stack itself.

The number of permeable discs/stacks present in the bio-reactor, or a module thereof, can be any number, preferably a number of from 2 to 100, such as 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and 100. The number of permeable discs/stacks is preferably an even number.

The bioreactor of the present invention may according to one embodiment comprise a porous matrix, one or more bio-reactor inlet port(s) and one or more bio-reactor outlet port(s),
wherein said matrix is suitable for anchoring and/or supporting the cultivation of living cells,
wherein said matrix separates said one or more bio-reactor inlet port(s) from said one or more bio-reactor outlet port(s),
wherein said matrix comprises individual matrix sections each separated by a spacer section for diverting feeding liquid to or from said individual matrix sections.

Each of such "individual matrix section" can comprise a plurality, as for example at least 2, "individual matrix sub-sections", wherein each such sub-section is separated from another sub-section by a permeable layer comprising a plurality of openings exerting a biological cell retaining function, but not a feeding liquid retaining function, wherein the diameter of the openings of the permeable layer is smaller than the diameter of the biological cells to be cultivated, thereby creating a layer in between individual matrix sub-sections which is capable of diverting feeding liquid in a direction essentially perpendicular to the direction in which feeding spacers and drainage spacers are diverting feeding liquid to and from, respectively, the individual matrix sections.

The thickness of an individual "permeable layer", or the collective thickness of a plurality of "permeable layers" dividing an individual matrix section into a plurality of sub-sections, is preferably less than 10% of the thickness of the individual matrix section comprising said one or more permeable layer(s). The one or more permeable layer(s) preferably divide an individual matrix section into sub-sections having at least essentially similar thicknesses, i.e. no sub-section differs in thickness by more than 10% from any other individual matrix sub-section.

The permeable layer(s), when present, ensures that feeding liquid can flow from a feeding liquid spacer either through the individual matrix sections, or through the permeable layer, thereby further reducing and/or eliminating gradients of feeding liquid nutrients in the bio-reactor. Without being bound by theory, it is believed that the flow rate of feeding liquid along the permeable layer will be faster than the flow rate of feeding liquid through the individual matrix parts. However, it is also possible that under some practical conditions of bio-reactor operation, the flow along flow rate of feeding liquid along the permeable layer will be slower than the flow rate of feeding liquid through the individual matrix parts. Under such practical circumstances the feeding liquid being diverted along the permeable layer can be regarded as a supplemental source of feeding liquid useful for obtaining and sustaining optimal biological growth conditions.

In one aspect of the present invention there is provided a bio-reactor comprising a plurality of permeable discs comprising a matrix comprising a plurality of fibres defining a plurality of inter-connected, open cells or pores extending through at least part and preferably all of each disc,
wherein biological cells are capable of adhering to the fibres and capable of residing in at least some and preferably all of the inter-connected, open cells,
wherein the plurality of permeable discs are alternately separated by feeding spacer sections and drainage spacer sections, respectively, so that each feeding spacer section provides feeding liquid to each of a first set of two adjacently located, permeable discs and so that each drainage spacer section receives feeding fluid from each of a second set of two, adjacently located, permeable discs,
wherein each disc is contacted by one feeding spacer section and one drainage spacer section, respectively, on opposite sides of the disc,
wherein essentially all feeding liquid entering the disc from the side of the disc on which the feeding spacer section is located is diverted through the disc and exits the disc on the opposite side of the disc, where the drainage spacer section is located.

The first set of two adjacently located, permeable discs and the second set of two adjacently located, permeable discs have one disc in common when the feeding spacer section and the drainage spacer section are positioned next to each other in the bio-reactor, i.e. when they contact opposite surfaces of one and the same disc.

The overall flow of a feeding liquid through each disc is essentially in a direction which is perpendicular to the direction of the flow of feeding liquid along the feeding spacer section feeding said disc, i.e. the matrix material of the disc exerts a "cross-flow" effect on the feeding liquid. Likewise, once feeding liquid exits a disc it is diverted along the drainage spacer section in a direction which is also essentially perpendicular to the direction of flow of feeding liquid through the disc.

The open cells or pores of the matrix of the permeable discs are larger in diameter than the biological cells to be cultivated, thereby allowing said cells to reside in said open cells during all or part of the duration of the fermentation.

The bio-reactor can be fitted with a suitable pump in order to ensure the a desirable flow rate is obtained. The bio-reactor can also be fitted with sensors and a control unit for controlling the seeding of cells and the progression of the subsequent fermentation.

In another aspect of the present invention there is provided a bio-reactor comprising a plurality of permeable discs or stacks comprising a matrix comprising a plurality of fibres defining a plurality of inter-connected, open cells or pores extending through at least part and preferably all of each disc, wherein biological cells are capable of adhering to the fibres and capable of residing in at least some and preferably all of the inter-connected, open cells, wherein the plurality of permeable discs are alternately separated by feeding spacer sections and drainage spacer sections, respectively, so that each feeding spacer section provides feeding liquid to each of two adjacently located, permeable discs and so that each drainage spacer section receives feeding fluid from each of two, adjacently located, permeable discs, i) a plurality of permeable discs comprising a matrix comprising a plurality of fibres defining a plurality of inter-connected, open cells or pores extending through at least part and preferably all of the disc, wherein biological cells are capable of adhering to the fibres and capable of residing in at least some of the inter-connected, open cells, wherein the plurality of permeable discs are alternately separated by feeding spacer sections and drainage spacer sections, respectively, so that each feeding spacer section provides feeding liquid to each of two adjacently located, permeable discs and so that each drainage spacer section receives feeding fluid from each of two, adjacently located, permeable discs, ii) one or more inlet ports for diverting a feeding liquid to one or more feeding tubes of the reactor, iii) one or more axially elongated feeding tubes comprising a plurality of openings through which feeding liquid can be diverted to each of the plurality of permeable discs, iv) a plurality of elongated and optionally cross-linked feeding spacers in liquid connection at a proximal end thereof with the one or more feeding tubes and extending in an essentially radial direction therefrom, wherein feeding liquid can be diverted from said one or more feeding tubes to said plurality of feeding spacers through said holes of said one or more feeding tubes, wherein the distal end of each feeding spacer is not connected to an outlet port for diverting feeding liquid to a collection reservoir, wherein each feeding spacer separates two adjacently positioned permeable discs, v) a plurality of elongated and optionally cross-linked drainage spacers in liquid connection at a distal end thereof with one or more outlet ports for diverting feeding liquid to a collection reservoir, wherein the plurality of drainage spacers are located essentially in parallel to the plurality of feeding spacers, wherein feeding liquid can be diverted from each of said plurality of feeding spacers and through a pair of neighbouring, permeable discs separated by a feeding spacer to one or more drainage spacers, wherein the distal end of each drainage spacer is not connected to a feeding tube hole, wherein each but end-positioned drainage spacer(s) separates two adjacently positioned permeable discs, vi) a wall section comprising a plurality of collection reservoir outlet ports, wherein each collection reservoir outlet port is in liquid contact with a collection reservoir, and vii) a collection reservoir for collecting feeding liquid diverted to said collection reservoir from the permeable discs via drainage spacers and through said collection reservoir outlet ports.

The bio-reactor design variations when the permeable discs are based on organic materials are e.g. such as:
1. Soft matrix bodies based on fibres
2. Semi matrix rigid bodies based on fibres, particulates, grains, spheres
3. Porous matrix envelopes both based on and encapsulating compacted fibre, particulate, grain, sphere, carriers The bio-reactor design variations when the permeable discs are based on in-organic materials are e.g. such as:
1. Rigid matrix bodies based on particles, grains, spheres
2. Semi rigid matrix bodies based on fibre and particles, grain, spheres
3. Porous matrix envelopes both based on and encapsulating compacted fibre, particulate, grain, sphere, carriers The bio-reactor according to the present invention can in one embodiment be in the form of a single-use design with disposable capability for most of the components used.

The bio-reactor according to the present invention is in one embodiment fully scalable from bench-top level (1-15 L) to at least "small scale production size" (100-1000 L).

The bio-reactor according to the present invention achieves in one embodiment an equipment volume reduction of least 20 or even 50 times compared to current suspension reactor bio material production capability.

The bio-reactor according to the present invention has in one embodiment a compact design for small foot print demand limited clean room facilities.

The bio-reactor according to the present invention is in one embodiment operated under conditions allowing an overall gradient free operation.

The bio-reactor according to the present invention achieves in one embodiment a fermentation based on a high cell density, such as more than $5 \times 10^8$ cells/mL (i.e. about 100 times better than today's average).

The bio-reactor according to the present invention achieves in one embodiment a production capability of more than 2 gram/liter/day for laboratory scale production and more than 10 gram/liter/day for a pilot scale production.

The bio-reactor according to the present invention can in one embodiment employ integrated single-use sensors, thereby promoting the bio-reactor as a "single-use" bio-reactor. Depending on the selected materials, the bio-reactor of the present invention can either be autoclaved, otherwise sterilized or, when for "single use", be disposed of.

Accordingly, in one aspect the present invention is directed to an environmentally friendly, single use, disposable bio-reactor. State-of-the-art single-use bio-container based bioreactors suffer from a number of draw-backs: Little proof of efficiency, no consideration of scaling, few systematic studies proving acceptable levels of leachables and extractables, absence of sensors, and finally no studies on the economics of converting multiple use systems to single-use systems.

As the market for single-use bio-reactors have matured over time and begun to address most of these issues, their market acceptance has rapidly expanded and a need exists for improved single use bio-reactors. When being designed for a single use application, the bio-reactor according to the present invention aims to achieve a number of objectives and the development of the single use bio-reactor according to the present invention is driven by a reduction or elimination of sterilisation and cleaning requirements, an improved plant flexibility, elimination of a costly CIP cleaning-in-place operation and the associated validation of the CIP process, as well as reduced costs and faster time to market for the end product.

All of the above-cited benefits have been documented for the bio-reactor according to the present invention. Additionally, the bio-reactor according to the present invention clears many of the hurdles required by CMO's (Contract Manufacturing Organisation). These hurdles include the ability to add reliable, accurate, low cost sensors, so that standards can be generated and the process repeatability readily documented. It is unlikely that these hurdles will be fully cleared by simply re-applying the traditional methodologies of stainless steel and glass vessels to single-use bio-reactors. The distinct differences in construction materials and methods of use dictate that new solutions should be sought, which augment the advantages of single-use systems such as the bio-reactor disclosed herein when designed for a "single use" operation. When being designed for a "single use" operation the bio-reactor preferably comprise materials which a re-cyclable, i.e. polymer based materials, rather than stainless steel and glass.

In one embodiment of the present invention the bio-reactor comprises stacked fibre based porous matrix sheets in the form of discs having a thickness ranging between 0.1 to 200 millimeter. The fibres have attractive surface properties for anchoring of biological cells thereto, and the matrix pore size can be about twice the size of the cells to be cultivated (i.e. a pore size of from about 5 to 100 μm). The matrix discs or sheets stacked in sets and are alternately separated by nutrient feed spacers and drainage flow spacers. Multiple sets of matrix sheets or discs can be "squeezed" into a flow friendly and compact design. The design can have a central nutrient feed tube and a circumferential drainage reservoir, or vice versa. All nutrients preferably pass equally through each $cm^2$ matrix wall section, thereby eliminating nutrient and gas gradients. The reactor core of the bio-reactor is preferably enclosed in a close coupled plastic bag with integrated single-use sensors. The fibres are preferably disposable, the sensors are also preferably disposable and the bag can also be disposable so that the bio-reactor can be designed for 100% single-use.

Linear scaling up from laboratory scale to "small scale production" reactors allows up-scaling from a one disc set-up being Ø47×L4 millimeter/6 $cm^3$ to a multi disc set-up Ø575× L1000 millimeter in high/150,000 $cm^3$ creating the impressive scaling number of 1:25,000. With volume reduction of 1:40 such larger reactor based on the present invention is equivalent to a suspension tank of 150,000×40=6 $m^3$. The smallest body though being possibly only one $cm^3$ and the largest being Ø1,000×L2,000 millimeter being app 1.5 $m^3$ creating the astonishing scaling number of 1:1,500,000.

In further embodiments nutrients and dissolved oxygen in the medium is preferably transported with no gradients through all the pores of the porous matrix of the employed discs to the micro organisms disposed on the surface and within the pores of the matrix. Each of the inlet feed channels (feeding spacers) in liquid contact with the feeding tube has no outlet port and thus cannot divert feeding liquid to a collection reservoir. The feeding spacers facilitate a forced flow of feeding liquid along the feeding spacer section in a direction away from the feeding tube(s), through the porous, permeable discs and further along an outlet channel (drainage spacer section) before entering a collection reservoir. The permeable discs of the bio-reactor have numerous porosity-determining, through-going pores, or open cells, permitting a free exchange of fluids and liquids from the carrier feed channels (feeding spacers) to drainage channels (drainage spacers). For bio-reactor applications the open pores within the porous matrix are preferably at least once or twice the size of the anchored biological cells, including micro-organisms. For separation applications, the opposite design with pores significant smaller than the micro organism applies.

The invented design solutions may find use within technical areas both within and outside the pharmaceutical industry, such as within the filtration, clarifying, retention and separation, cleaning, up-concentration, sterilization, ion-exchange. The presented design is further functional as a dept filter comprising an asymmetrical pore structure and/or an asymmetrically arranged fibre thickness creating a gradient density matrix.

DEFINITIONS RELEVANT FOR THE PRESENT INVENTION

Bio-reactor or fermenter—a physical device, container, vessel which support biologically active environment and houses micro organism performing a process Fermentation—an industrial process which refers to highly oxygenated and aerobic growth conditions typical operating in batch mode Bag—a flexible container made from 0.1-0.2 clear plastic foil also used as bio-reactor Batch—a bio-reactor to which no fresh medium is added and no cultured liquid removed Fed-batch—a bio-reactor to which fresh medium is added and no cultured liquid removed Perfusion mode operation—operation principle for a bioreactor, the media is continuously exchanged, fresh nutrients added and product is harvested throughout the culture period Cross flow mode operation—operation principle for a bio-reactor and separation unit Micro organism—microbes, cells such as; bacteria, fungi, algae, plankton, enzymes, animal, mammalian, tissue, yeast, plant, insect, protozoa, prokaryotic, eukaryotic, archaea Anchorage dependent—cultivation of micro organism anchored onto a surface Suspension dependent—cultivation of micro organism, cell lines suspended in liquids Growth media, nutrient—fluid containing water, carbon source, oxygen, vitamins, etc.

Membrane—a layer of material, which serves as a selective barrier between two phases and remains impermeable to specific particles, molecules, or substances when exposed to the action of a driving force.

Separation—dividing fluid borne particles of different size by membrane filtration into at least two separate fluid streams Filtration—mechanical method to separate solids from liquids or gases by passing the feed stream through a porous sheet such as a membrane, which retains the solids and allows the liquid to pass through.

Purification—physical separation of a chemical substance of interest—typically performed after, downstream of the bio-reactor in order to separate the product (proteins) from waste (used cells, damaged cells)

Chromatography—Size Exclusion Chromatography—a device that holds chromatographic packing material, often the final step in a purification process. SEC works by trapping these smaller molecules in the pores of a particle. The larger molecules simply pass by the pores as they are too large to enter the pores.

Disposable—products manufactured from organic materials

Porosity—is a measure of the void spaces in a material expressed in percent 0-100%

Macro pore size—ranging 10-500 µm

Meso pore size—ranging between 1-10 µm

Micro pore size—ranging below 1 µm

Non-woven—is a fabric-like flat porous sheets made from fibers, bonded together by chemical, mechanical, heat treatment, such as felt, which are neither woven nor knitted Honeycomb body—a one piece body manufactured typically from ceramics Column—a series of capsules stacked on top of each other

BRIEF DESCRIPTION TO THE DRAWINGS

FIG. 1—The bioreactor in its most simple form in a flexible plastic bag

Figure 2:
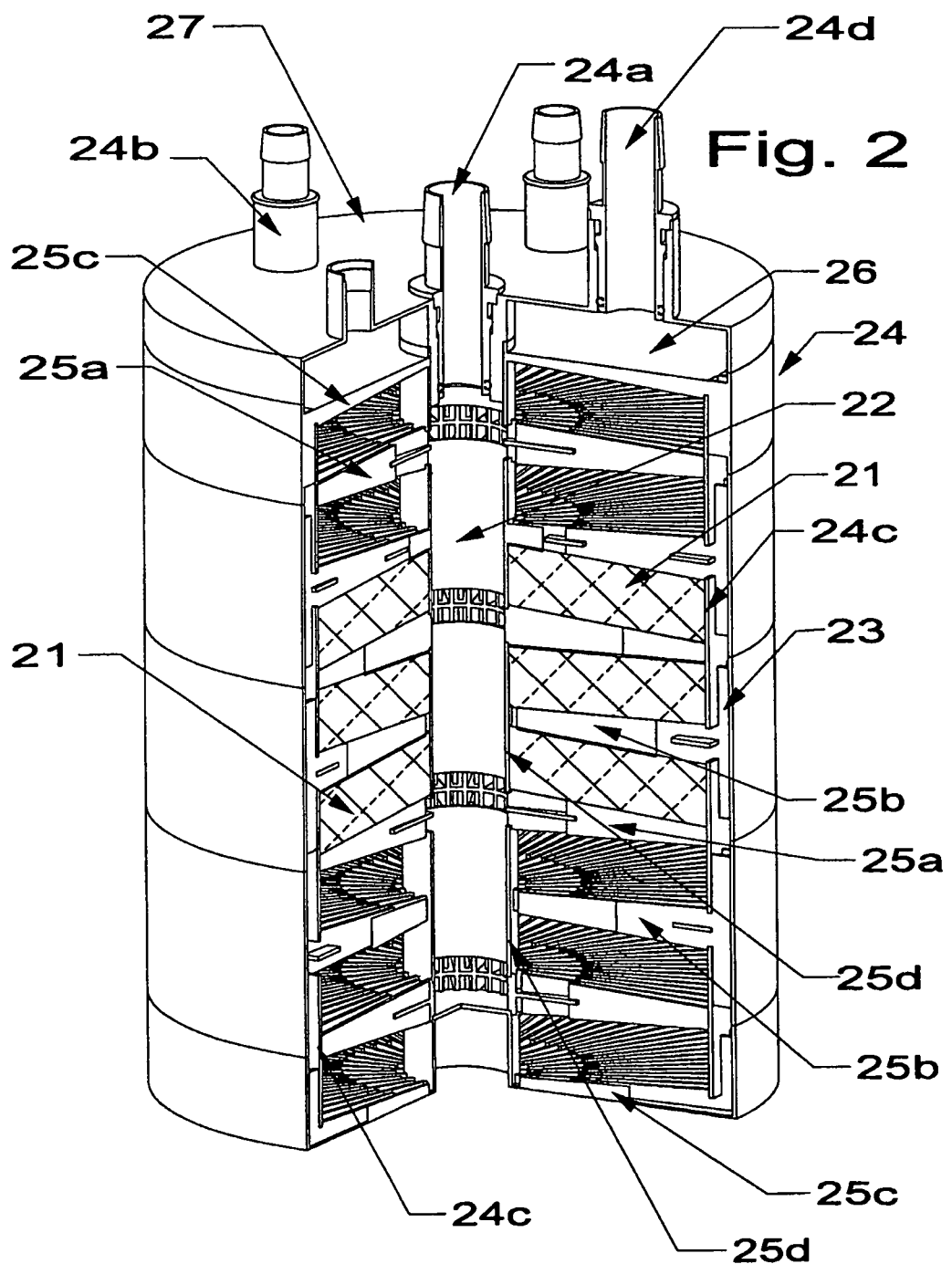

FIG. 2—The bioreactor housed in a rigid plastic cylinder

FIG. 3—The bioreactor integrated between two diaphragm pump modules

FIG. 4—A bioreactor based on envelopes covering a backed bed

FIG. 5—A bioreactor integrated with a capsule

FIG. 6—A pleated bioreactor

FIG. 7—A spiral bioreactor

FIG. 8—A square channel bioreactor seen in perspective

FIG. 9—A square channel bioreactor seen in cross section

Figure 10:
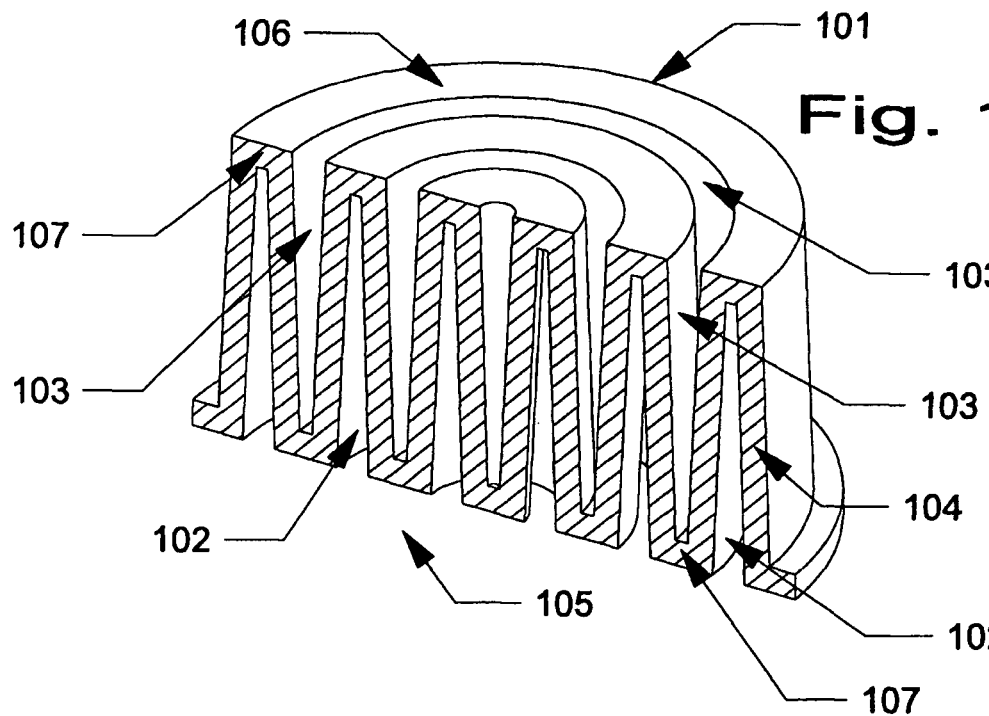

FIG. 10—A circular channel bioreactor seen in perspective

FIG. 11—A circular channel bioreactor seen in cross section

Figure 12:
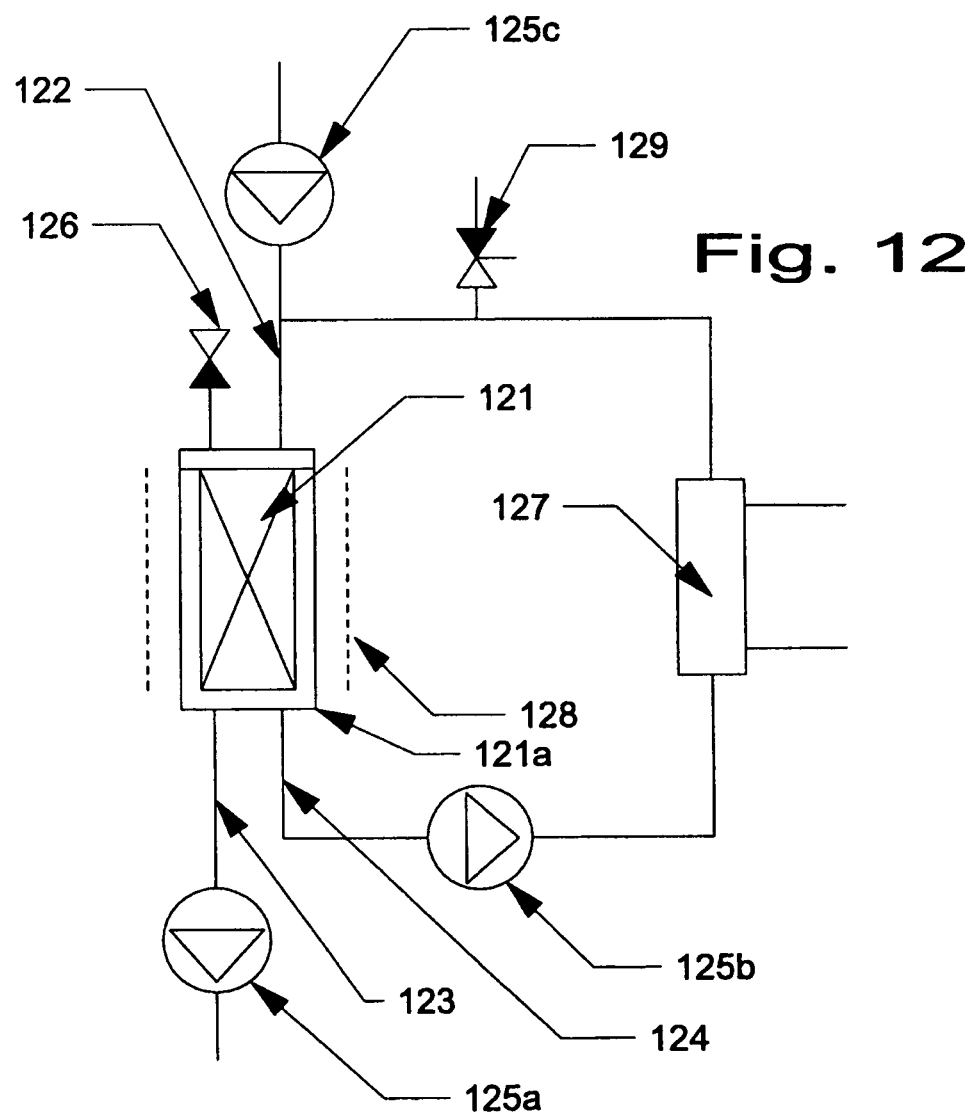

FIG. 12—A method of operation

FIG. 13—A method of operation

DETAILED DESCRIPTION OF THE INVENTION

The present invention in one embodiment (version 1=matrix sections, such as discs) features multiply stacked and in parallel operating permeable matrix sections preferably having a semi-deep bed configuration and an attractive internal surface area based on compacted fibres assembled into a single matrix core (FIG. 1, 2, 3, 4).

The matrix is in one embodiment based on polyester fibres stabled into non-woven felt as manufactured e.g. by FiberTex A/S, Denmark or DelStar, Inc from the United States. Non-woven sheets can be cut, shaped into matrix sections that are essentially circular or has any other shape.

Sheet thickness can range from e.g. less than 1 millimeter to 50 millimeter or more, such as e.g. from 2 millimeter to 20 millimeter. The fibre diameter can range e.g. from less than 0.1 µm to more than 100 µm, such as e.g. from 1 µm to about 100 µm. The resulting packing density of a matrix section can e.g. be in the range of from 250 to 4,000 gram/m$^2$—corresponding an internal matrix surface area of about 50 to 1,500 m$^2$/m$^2$ for a 10 millimeter thick matrix section.

More than two fibre sheets can be stacked, thereby forming a matrix section, which matrix section can again be stacked in a multi matrix section set-up. The matrix sections in the stack of individual matrix sections can be the same or different matrix sections and the individual matrix sections can have the same or different properties. The same or different properties can affect e.g. properties such as gradient densities, or gradient fibre thickness through the matrix to obtain asymmetric matrix properties or just suitable thickness. Also, the individual fibre sheets or matrix sections can be manufactured with asymmetric pore size properties perpendicular to the individual fibre sheets.

Feeding liquid is diverted to the bio-reactor through an inlet port and initially enters a feeding tube in liquid contact with a plurality of individual matrix sections via a plurality of spacer sections capable of diverting feeding liquid exiting the feeding tube through a plurality of holes therein to the matrix section of the bio-reactor.

Liquid feeding medium is diverted at least partly and in some embodiment entirely by means of hydraulic forces through the matrix and comes into contact with the biological cells residing within the porous matrix sections. These matrix sections typically comprise at least one three-dimensional porous matrix having an open pore volume e.g. of from 15% to 95%, such as from 20% to 85%, for example from 30% to 80%, such as from 40% to 80%. The open pore volume is accounted for by open pores having an average diameter e.g. of from 5 to 500 µm, such as from 10 to 100 µm. An open pore, also termed an open cell, is defined by a pore (or cell) capable of establishing a liquid connection between spacer sections located on opposite sites of an individual matrix section. Two such oppositely located spacer sections are termed corresponding or operable linked feeding spacer section and drainage spacer sections. The correspondence occurs when feeding liquid diverted to an individual matrix section by a feeding spacer (section) is subsequently—following passage of the matrix section in question—diverted away from the matrix section by a drainage spacer (section).

The size of the matrix sections is not limited to any particular diameter or surface area and in one embodiment the present invention is directed to matrix sections having a diameter of about 1000 millimeter in diameter or 0.5 m$^2$ in area. Matrix section thickness may vary from a few millimeters to preferably less than 250 millimeter, such as preferably less than 200 millimeter, for example preferably less than 15) 0 millimeter, though a thickness ranging from 5 to 50 millimeter, such as from 10 to 30 millimeter is according to one presently preferred hypothesis believed to be more relevant.

The bio-reactor in one embodiment comprises a number of identical, or differently shaped, stacked matrix sections and has e.g. a central inlet and a circumferential outlet assembled in a fluid tight housing. However, the opposite orientation is also possible, i.e. a circumferential inlet and a central outlet assembled in a fluid tight housing.

The preferably non-woven matrix sections are separated by spacer sections for liquid flow distribution, i.e. for both feed and drainage of feeding liquid. Feeding spacers and drainage spacers are sealed in opposite ends, respectively, to achieve flow direction control. This design has been found to provide an extraordinary uniform deposition of the introduced (seeded) biological cells, such as micro organisms, and most important—the design has been found to provide a uniform flow distribution.

In one embodiment of the present invention, the individual matrix sections are stacked on top of each other and separated by spacers on both the inlet side and on the circumferential side. This design creates a symmetrical and parallel arrangement so that the spacers located between different matrix sections correspond with and, under practical circumstances, is in liquid contact with, both one or more inlet port(s) and one or more outlet port(s) which are isolated from the inlet port(s) and/or from the matrix sections by said spacers. The drainage spacer sections located on the "outlet side" of the matrix sections communicate with and are in liquid contact with a common collection volume e.g. located at the circumference, such as e.g. in a cavity of the encapsulation of the bio-reactor.

Nutrients and fresh media to the biological cells, such as micro organisms, are introduced into the bio-reactor via one or more inlet ports and pumped through the reactor constantly to the circumference exit of the reactor.

Preferably non-woven, porous matrix sections stacked and laminated with feeding spacer sections and drainage spacer sections provide as much as up to 20 to 40 times more surface area to bio-reactor volume. The example is a conventional, industrial stainless steel vessel having an internal diameter of 300 millimeter and a length of 1000 millimeter and approx. 70 liter of volume. With matrix sections packed to 50% of the packing density (more than 20 $m^2$/liter surface area) of a 140 liter container, the total surface area for anchoring micro organisms is an impressive 20×70=1,400 $m^2$.

The matrix sections is in one embodiment stacked around one or more centrally located feeding tube(s) which supplies feeding liquid comprising nutrients required for biological cell cultivation to the feeding spacers through a plurality of holes or openings or feeding liquid outlet port(s) located in said one or more centrally located feeding tube(s). The feeding spacer sections provide feeding liquid to the matrix sections which in turn ensure an optimised radial and orbital flow pattern of the feeding liquid. The centrally located feeding tube(s) can also supply oxygen and distributes the oxygen efficiently, thereby solving the gradient problems which are typically a limiting factor when performing bio-fermentations. The concept of stacking the individual matrix sections allows significant matrix diameters and matrix heights to be employed while at the same time having a control of feeding liquid distribution and drainage.

The matrix sections can also, in one embodiment, be covered by or surrounded by independent membranes based on thin sheets having a pore size less than that of the preferred, biological cells to be cultivated. The membrane(s) are alternatively mounted on the outlet side of each matrix section—thereby creating a pressure drop eliminating nutrient concentration gradients across the inlet matrix section side—and thereby eliminating such gradients from the entire matrix surface.

The matrix sections or cassettes comprising such sections can alternatively be assembled into a supporting base, a cartridge or a housing e.g. having a central inlet and a circumferential outlet. Such matrix sections can be fabricated from fibres of e.g. non-woven materials, polymers, ceramics, metals, and celluloses with or without an integrated, high pressure drop membrane.

Feed and drainage spacers can e.g. be a layer of flow-net, screens, corrugated sheets, netting, rib stiffener, set of ribs, matrix section with a radial set of ribs having suitable (edge) flow characteristics=excellent liquid flow along and within the thickness of the spacer. Spacers may be layers of flow-nets, screens, and corrugated sheets, nettings assembled with different properties creating an asymmetric structure. Hereby the pressure drop along the feed and drainage layer is considerably lower than the pressure drop perpendicular to and through the matrix. Materials may also be of hydrophobic character to avoid fouling, trapping of micro organisms.

Some extruded flat flow-net separators may have a first set of parallel strands and a second set of parallel strands intersection the first set of strand at an angle. And be extruded polymer mesh from companies like Nalle Plastics Inc or DelStar Inc or Industrial Netting Inc. all located in USA or Mallanet from Spain. Extruded flow-net are characterised by their thickness (range 0.1-4 millimeter), by the number of strands per inch (2-64), mesh per inch (MPI), hole size (0.2-50 millimeter) and open area.

Alternatively the flow-net may be expanded sheet materials made by a process of slit and stretch performed by Dexmet Corp in USA and characterised by the material thickness, number of strands per inch, strand width, mesh per inch (MPI), openings per $in^2$, and open area. Both flow-net examples corrugated for high flow capabilities and potentially laminated with flat and fine pored spacers on each side in order to avoid intrusion of the matrix core materials. In particular for FIGS. 1, 6, 7, such lamination method is highly suitable. FIG. 6 is a pleated type of design with the pleats arranged both curved and combined radial and symmetrical around the centre line from which spacers extent.

Alternatively, the spacer may be a cast, moulded device round, rectangular, square or of any shape for lamination of the individual matrix sections. Examples include a round feed spacer e.g. based on a radial rib design thicker at the feed entrance and thinner closer to the collection volume entity. The drainage spacers are of the "opposite" design—i.e. thinner at the feed entrance and thicker closer to the collection volume entity.

Spacers preferably include seals, connections, mechanical support etc. for stacking purposes. Spacers can e.g. be cast bodies with rib design, channel design, pore size, material shape and choice with design specifically to be laminated with matrix sheets. Such as being part of description in FIGS. 2, 3, 4 and 5.

Flow net spacers could alternatively be designed with ribs and fluid flow paths suitable for integration during production of the porous matrix and hereby be fully embedded. The purpose is to simultaneously give mechanical support to the structure and act as either or both feed and drainage spacers for the fluid to pass the porous matrix of the embodiment. Fluid inlet and outlet in particular arranged at each end face and hereby different to known cylindrical pleated filters with inlet, outlet on the inner or outer surface of such a cylindrical body. The spacer hereby becomes a one time, single-use mould and by being embedded into the overall embodiment participates potentially optimum in the fluid distribution.

Flow net or similar structures may be integrated inside, embedded inside the non-woven matrix or between layers of woven matrix in order to obtain a specific rigid appearance. Such a design is seen from German Fortron named PPS with difference in fibre thickness of at least 1:10 preferably higher. Layers of non-woven and woven materials may further be oriented according to need and are not limited in any method of assembling.

Alternatively the spacers, or parts of the spacers, may be manufactured from natural vegetable organic materials for natural re-cycling purposes after its use.

In general, the physical dimensions of the spacer sections are determined by the size of the practical circumstances characterising a particular cultivation of biological cells. If the bio-reactor is manufactured with a large diameter, the feed inlet in operable liquid contact with a spacer section must be larger than a feed inlet in operable liquid contact with a spacer section when a smaller diameter bio-reactor is used.

The present invention (version 2=envelope) features further the variation of the single-use bioreactor cassettes containing the single-use porous matrix enclosed inside an envelope (FIG. 4). The envelope is preferably a rotation symmetrical, a circular box, container of trapeze alike cross section with at least one wall constituting a rigid or a flexible porous membrane with pores of a size suitable to retain the packed bed of fibres, grains, spheres, Rasching bodies or growth bodies in general for a bed thickness of 5-250 millimeter, preferably ranging 8-150 millimeter such as 10-50 millimeter. The envelope walls, if based on textiles, fabrics or non-woven materials, are sewed with thread, from various pieces of sheet into said envelope shape while integrating and fully inclosing the packed bed material. Two envelopes may share the same symmetrical feed spacer and by further joining the flexible porous membrane at least at the circumference of both envelopes, creating a stackable envelope unit by encapsulating the feed spacer. The envelope membranes, walls may be a polymeric material cast into shape or a pre-shaped sheet of polymeric based material with macro-pores or even holes in said membranes or wall able to retain the packed bed material.

Alternatively the drainage spacer is encapsulated or both feed and drainage spacers are encapsulated. On the feed side of the envelopes, before the packed bed, spacer devices insure even radial flow pattern to the twin packed beds simultaneously. The envelope walls on the drainage side of the twin packed beds are next to a radial fluid collection volume, which continue the radial flow pattern from the twin packed beds simultaneously. The envelope membranes are in no way limited to have parallel walls or being of flat design. Multiple envelope bodies may be stacked inside a vessel or a disposable capsule.

Further one way of manufacturing such envelope bodies is by packing a suitable amount of powder mixture material and/or fibres into a casting mould offering some handling strength before the stack assembling. Or multiple porous packing bodies arranged randomly between the porous membranes creating an envelope before the membranes are fixed at the edges. Two such envelopes are arranged on each side of and share a non restricted central feed spacer. One such envelopes further shares drainage spacer as a non restricted common outlet with the neighbour envelope.

The design of the bioreactor device with the porous matrix envelope allows micro organisms to travel into the interior of the bioreactor packed deep bed matrix. The bodies inside the envelope preferably have a large porosity combined with the required large surface area suitable for anchoring micro organisms. If chosen the pores in the drainage membrane, down stream side of the packed bed, is of a different size compared to the feed membrane, which restricts both the growth bodies and partially the micro organisms from leaving the bioreactor envelope, but not the product. Or other desired function of the outlet membrane(s) may be obtained. Envelope dimension may range 100-1,000 millimeters in diameter and an envelope unit height of 10-300 millimeters before stacking and feed and/or drainage spacer integration.

The present invention in one embodiment (version 3=pleated) is also directed to a pleated bio-reactor alternative in design based on pleating of a non-woven sheet matrix into a compact reactor (FIG. 6). A pleat is a type of fold formed by doubling fabric, sheets backed upon itself and securing it in place. Pleating is a compact method of obtaining high loads of fabric, porous sheets and used extensively in the filtration industry and the manufacturing method is often called knife pleat. If order to avoid each pleat gets in contact to the neighbour pleat separators, spacers with fluid capability are arranged between the pleats. The pleat matrix thickness is selected in order to get the desired flow and pressure drop over the matrix. The pleat will typically be of the same thickness all through the core. The pleats are typically arranged on the straight radial lines of the cylindrical core though higher pleat density is obtained if the lines are curved and not starting from the core centre. Two individual diameter pleated bodies may be arranged into the same housing with one pleated body surrounding the other with the upstream volume shared, being in between the two bodies so one downstream becomes the centre of the in diameter smaller body and the other downstream the circumference of the in diameter larger body. Module dimensions ranging 50-500 millimeter in diameter with length of 200-2,000 millimeter though preferable 500-1,000 millimeter in length.

The present invention in one embodiment (version 4=spiral) is directed to a spiral bio-reactor being of cylindrical and elongated design with a series of parallel oriented dual spiral layers of non-woven matrix sheets laminating the drainage channel spacers and on each side in contact with the feed channel spacers all wound around a central perforated fluid collection tube (FIG. 7). The drainage spacer is shorter and less wide than the matrix sheet and on three sides sealed from the feed stream with seals between and/or bonding of the matrix sheet edges, which hereby form an envelope around the drainage spacer, though the drainage spacer is open to, connected to and in unhindered permeate fluid correspondence with the perforated fluid collection tube. The feed spacers are open on all four edge sides and with no fluid connection to the fluid collection tube receiving the permeate. Anti-telescopic members are mounted at both end surfaces of the sandwich like circular core matrix.

Typically operating in cross-flow mode with longitudinal flow, the feed are supplied from one end face being conveyed in axially direction inside the coarse and somewhat thick feed spacers to the opposite end face exiting as retentate. A slight over pressure drives the fluid perpendicular to and through the matrix core collected on the other side of the matrix by the drainages spacers conveying the permeate fluids tangential to the central collection tube where the drainage spacers are anchored. The element is to be fitted inside a low pressure container being fabricated from rigid or flexible materials. More than one element may be fitted into the same container in series, after each other and share the central collection tube permeate fluid exit. Alternatively the core is not fitted tight inside a tube, but with free feed or head space around the core circumference and in longitudinal direction allowing the feed stream to enter the feed spacers perpendicular to the core. Compared to the typical and in the industry well known spiral wound membrane filter, which need to fulfil high demands to trapping efficiencies, the spiral-bio-reactor has low demands to filtration efficiency. Module dimension ranging 50-250 millimeter in diameter and length 200-1500 millimeter preferable 100-500 millimeter.

The present invention in one embodiment (version 5=cast bodies) is directed to a rigid foam based core matrix structure. The cast foam core bodies may take any shape, thickness as discussed in other parts of the present invention. Such as discs shaped, plate shaped, saucer shape, honeycomb shaped. Be single and double density biopolymer foams, composite biopolymer foams including both single and double density foams.

Solid foams form an important class of lightweight cellular engineering materials. These foams can be classified into two types based on their pore structure. The first type of foams is called open cell structured foams. These foams contain pores that are connected to each other and form an interconnected network which is relatively soft. The second type of foams does not have interconnected pores and are called closed cell foams.

The foam may be semi rigid or soft bodies based on pure natural sponges from the in sea living marine organism such as *Spongia officinalis*, or fresh water sponges like *Spongilla lacustris*. Foam structures based on traditional manufacturing methods where polyurethane foam are exposed to and impregnated with a ceramic fine grained slurry followed by drying and high temperature firing. Specification of the hereby negative skeleton are typically with a maximum of 100 ppi (pores per inch) corresponding to pores as small as 0.5 millimeter in diameter.

A new and promising process for fabricating ceramic foams or calcium phosphate containing foams pass a route of stable, well-dispersed, high solids content, aqueous ceramic suspension is prepared which also incorporates an acrylate monomer together with an initiator and catalyst. The latter is used to provide in-situ polymerisation. After the further addition of a foaming agent, a high shear mixer is used to provide simple mechanical agitation that result in the formation of wet ceramic foam that can be dried and then fired. Foams can now be produced with largest pores 1 millimeter and densities as high as 30% of theoretical, whilst 20% dense foams have been produced with pores as small as 20-50 µm. Bio ceramic containing foams are known for promoting cell growth and being bio friendly in the bio medical industry.

The present invention in one embodiment is directed to a body (version 6=cast bodies) with a set of inlet channels and outlet channels. Traditional honeycomb bodies are all characterised by thin walls with limited wall porosity and channels as small as possible measured in CPSI—cells/channels per square inch—being in the range of 100 to 600 cpsi. In specific traditional flow-through honeycomb bodies are designed only for fluid flows along the channel and not trans/through the wall—and in specific not for growing micro organisms within the wall matrix. One embodiments of the present invention is a honeycomb body which differs vastly from traditional honeycombs exhibiting unusual thick walls and wide channels and high internal surface area within the wall matrix highly suitable for biofilm anchoring. Also the present invention takes advantage of the Wall-Flow-Filter principle. The media, fluid passing through the bioreactor differs from known technology as the fluid, the medium is passing through the wall matrix. Furthermore the very low media flow through such bioreactor preferably sees a relatively higher pressure drop when combining a membrane with said porous wall matrix. As the added membrane with significant higher pressure drop support an even fluid flow all over the inlet wall surface area. The reduced nutrient content gradient improves the yield of the present invention significantly. Pore size in the three-dimension matrix operating as a the invented bio-reactor ranging 1-500 µm preferably 10-50 µm creating 10-100 $m^2$ internal wall surface area per liter matrix. Porosity ranging 30-80% in the matrix if the said bio-reactor is fabricated from grain particles though often with practical porosity ranging 40-60%. The coarse matrix gives permeability ranging 0.1-10 Darcy preferably closer to 1-5 Darcy. Also it is very advantageous to have thick walls for optimum internal surface area such as FIG. 9.

Otherwise the wall thickness may be e.g. 1-150 millimeter, preferably 5-50 millimeter. The cell pitch, which is the combined measured figure in millimeters of the wall thickness and the channel width, may be in the range of 1-75 millimeter, preferably 5-30 millimeter. In one embodiment the bio-reactor will in a single body designed with 0.1-10 cpsi (cells per square inch) configuration and outer dimension of Ø144× L152 millimeter offer the volume of ~2.4 liter. For the conical channel cast version cell density may range from 0.1-5 cpsi with non circular channels. Bodies like FIG. 10 are not measured via cells per square inch.

A significant feature of the present invention is the three-dimensional very thick porous walls to which potentially membranes are adhered. Conventional wall-flow-filter or cross-flow-filtration devices preferably have very thin walls in order to minimise wall and/or trans-membrane pressure drop. A pressure drop comparison between the high volume flow wall-flow-filter and cross-flow-filtration with the present invention reveal difference.

One way of manufacturing such rigid carrier body is obtained by pressure casting, vacuum casting supported by vibration or pressing particles into the desired shape followed by sintering a bi-modal powder mixture comprising coarse-grain material and a fine-grain substance melting at a higher-than-sintering temperature gluing the coarse grains together in the contacts points.

Alternatively ways of manufacturing such rigid carrier body is obtained by casting or pressing mono-modal particles into the desired shape followed by sintering the powder mixture at higher-than-melting temperature gluing the grains together in the contacts points.

The channels of the typical extruded honeycomb body are limited to exclusively parallel wall design as obtained from the extrusion process. Better gradient eliminating design is obtained by conical channels with larger free end face openings and conical walls towards the end of the particular channel, but such design needs to be cast, slip cast, pressed, vacuum cast, etc. The design in order to optimise, exclude environmental gradients along the channels and through the channel separating walls. Both the feed and drainage channels being conical along the body may be round, square, hexagonal, octagonal or any other shape which offer identical wall thickness anywhere in the body. Further both the feed and drainage channel form may be mixed into any desired design.

The present invention in one embodiment is directed to a design of porous discs (version 7=cast bodies) with pore size in the three-dimension matrix ranging 1-500 µm preferably 10-50 µm. Porosity ranging 30-95% in the matrix if the bio-reactor is fabricated from fibres, often practical porosity ranging 40-90%. The discs arranged towards each other in sets forming feed spaces and drainage space as illustrated in FIG. 4. Cast from either powder based material or from fibre based materials or both combined. Assembling sets of the discs by stacking create the bio-reactor device to be housed in a standard stainless steel dome covered system with bottom plate which contains inlet and outlet. If manufactured from fibres methods are known under the names knitting, weaving, and braiding potentially followed by a gently sintering process, which increase mechanical strength of the discs. Also mixing of metal fibres with organic fibres is known as multifilament yarns in the industry. Such multifilament yarns will give interesting properties with partly electrical conductivity allowing selectable charging of the mesh.

The present invention in one embodiment is directed to a body (version 8=cast bodies) with a set of inlet channels and outlet channels manufactured by vacuum forming, such as when a porous mould is exposed to, dipped into a volume of and in contact with a suspension including flocculated fibres.

Low pressure on the back side of the perforated surface convey the carrying suspension, slurry to flow towards and through the mould where the fluid are drained through the porous screen, retaining the fibres which is collected and deposited on the mould surface. Exposure time to casting, suspension strength determine the thickness of the accumulated fibrous matrix body on the mould surface. After the vacuum casting process the body is removed and the remaining fluid is finally removed by drying and the body appear semi rigid. Typically a binder system is mixed into the suspension in order to facilitate anchoring the fibres internally for higher product stiffness. The initial vacuum casting process may be followed by further similar process in order to obtain asymmetric matrix properties. The matrix may for improved mechanical strength include a skeleton of pre-shaped thicker fibre or thread based mesh arranged prior to the vacuum casting process so the mesh becomes fully embedded in the structure after the vacuum casting process.

Further ways of improving mechanical strength after the vacuum casting method is possible by adding resins or by heat treatment. Such heat treatment may further shrink the body hereby reducing the pore size.

Making up such body will follow the alternative procedure, which is here described with particular reference to the embodiment illustrated in FIG. 4, 9 by uni-axial pressing such as when a set of moulds is exposed to a fluid suspension containing at least one type of fibres and possible binders and/or resins. A suitable volume of the suspension is allowed to flow into the casting cylinder for uniform settling containing at least one mould pistons. The suspension may be kept floating by gas introduced added from the bottom piston in order to improve suspension uniformity. The gas added under pressure from a series of holes in the piston or cylindrical wall. After filling the open casting chamber with suspension the top mould piston is moved into, closing the cylinder. At least one of the mould pistons is manufactured from macro porous materials, perforated or supplied with a multiple small drilled holes or variations thereof, which allow the suspension fluid passes out through the two pistons. While forcing the two pistons towards each other the fibres left in the cylinder is orienting and compacting to an embodiment of desired design. After the moulded article has obtained final shape the soft felt embodiment is removed from the casting machine and the remaining fluid is removed by drying until the body appear semi rigid.

Typically a binder system is mixed into the suspension of fibres in order to permanently anchor, adhere, bond the fibres at their contact points for higher embodiment stiffness. Alternatively the semi finished matrix embodiment after casting is further impregnated, exposed to a binder system dispersed, diluted in an aqueous solution for a soaking time based on wall thickness. The binder system may be cured by temperature, UV lights, reacting with a catalyst, etc. bonding the fibres together.

Pore size in the three-dimension matrix ranging 0.001-500 µm. For depth filter applications the pores range 0.01 to 10 µm pore size. For bio-reactor purpose the pores are preferably 10-100 µm creating 10-250 $m^2$ internal wall surface area per liter matrix. Porosity is ranging 40-95% in such matrix and if fabricated from fibres of various spec, often practical porosity range 60-90%.

The above variation of the present invention is only limited in dimension by manufacturing restrictions. Parts of the above may be sandwiched in order to obtain combined properties. Any of the above embodiments may have asymmetric pore structure carried out by methods well known in the industry.

Organic membranes—the possible extra membrane(s) mounted on the outlet side of the matrix outlet surfaces which hereby create further pressure drop. This effort in order to further reduce nutrient concentration gradients across the matrix and in specific the surface of the entire three-dimension matrix. The micro organisms hereby anchored inside the three-dimension matrix before the membrane(s) creating a biotech growth method for continuous protein expression and micro organism separator in just one system.

Outlet membrane with pores ranging selectively insures the cells, micro organism or biofilm do not penetrate the growth body, but only the product and nutrient pass the membrane mounted on the drainage side. The membrane(s) permeability is in the range of 1-100 times less than the three-dimension matrix being the wall. The membrane is designed from particles and/or fibres creating a smaller pore size than the growth body and applied on the fluid outlet side surfaces of the carrier body with macro pores, the membrane having pore diameter of 0.001-20 µm. Typically, such membrane is required when separating or allowing very small particles or suspended matter only to pass the membrane attached to the inlet side of the carrier. For the present invention the purpose of the membrane is opposite and works backwards as the membrane is attached to the outlet, drainage side which prevents release of anchored particles or cells oriented carefully inside the porous matrix—and only the product from the cells are allowed to pass the membrane. This principle is advantageous as the micro organisms are not removed from the interior of the carrier body.

In-organic membranes—the honeycomb and cast body design of the invention may be combined with a separating micro porous membrane(s) for selective passage of particles and fluids. The possible extra membrane(s) mounted on the outlet side of the matrix outlet surfaces and hereby created pressure drop eliminate nutrient concentration gradients across the matrix and the entire three-dimension matrix surface. The micro organisms hereby anchored inside the three-dimension matrix before the membrane(s) creating a biotech growth method for continuous protein expression and micro organism separator in just one system.

Outlet membrane with pores, holes ranging selectively from 5 to 10,000 nm sizes insures the cells, micro organism or particles do not penetrate the body, but only the product and nutrient does. The membrane(s) permeability being in the range of 1-100 times less than the carrier, the three-dimension matrix of the wall. A membrane may be designed from particles or fibres creating a smaller pore size than the growth body and applied on the fluid outlet side surfaces of the carrier body with micro pores having a diameter, size of 0.001-10 μm. The asymmetrical membrane applying a pressure drop being at least one order of magnitude higher than the pressure drop obtained from the carrier. The membrane material selected may be determined from its Zeta potential. Some materials like Zeolites may easily be altered. Membrane with pore sizes smaller than pores of the carrier body material deposited on the membrane carrier increases the separation efficiency of the device. This membrane also prevents particles from exiting the porous carrier. Typically, such membrane is required when separating or allowing very small particles or suspended matter only to pass the membrane. For the present invention the purpose of the membrane is opposite and works backwards—the outlet, drainage side mounted membrane prevents release of anchored particles or cells oriented carefully inside the porous matrix—and only the product from the cells are allowed to pass the membrane. This principle is advantageous as the micro organisms are not removed from the interior of the carrier body.

Hereinafter, the term "ceramic bio-reactor device" encompasses a porous monolith support for both the active micro organisms as well as potentially the membrane device and then the term "bio-reactor" encompasses permeate extracted from a membrane device. Such membranes can include separation barriers suitable for micro-filtration, ultra-filtration, nano-filtration in order to be selective to the inclusions in the permeate.

Reactor Design

The invention is not limited by dimensions or in any way to a symmetrical shape. The core may be of non cylindrical design, inlet volume shape or outside shape may be independently different with non parallel sides, trapeze design as yet an input for flow distribution control and gradient elimination. Asymmetrical matrix assembly with decreasing pore size perpendicular to the disc may further be combined with the shape for flow distribution control purposes. Bodies, discs or envelopes with different properties, different materials may be stacked in any order and thickness.

When the invention is designed into a disposable plastic bag construction the container may further house a heating element or temperature conditioning devise as well as appropriate sensors. A heating element may also be located within the inlet volume fully surrounded by the fluids to pass the core. In large bio-reactor systems the heating elements may further be oriented within the spacers preferably be integrated with the inlet zone spacers.

Housing Design

The bio-reactor core is preferably enclosed inside a bag made by flexible bio compatible polymers, plastics as housing with connected silicon or plastic hoses and/or flanges. The plastic bag enclosure is an alternative design with the purpose of being disposable and of a relatively low cost. The plastic bag is semi rigid as the reactor is both compact, but also of fixed dimensions and rigid. With a tight fit for the plastic bag around the matrix core the complete set-up becomes self supportive and need no extra external support like empty single-use plastic bags, which all need a container as support. The plastics selected offer low levels of leachable and extractable compounds. Plastic foil sheets formed into desired size, shape and by one or several of various welding methods seamed at the edges into a liquid tight container around the bioreactor.

More rigid plastics based capsules systems, self supportive design will allow for stacking purposes and may on the outside appear symmetrical and the core on the inside may be asymmetrical. Stacking will be arranging the capsules next to each other with inter-connecting fluid exchange flanges sealed insuring liquid tight performance. Improved mechanical strength for plastic parts is well known in the industry by adding fibres to the hot plastic during forming. Also electrical properties can be altered by specific substances added to the polymers.

The disposable capsules may be of tangential flow principle, radial flow principle, cross flow principle with symmetric or asymmetric porous matrix core design and either of round design, rectangular or combinations hereof.

Yet a variation is non round capsules or cassettes with at least one fluid inlet and at least one fluid outlet integrated within the capsules overall design. Such as the Plate & Frame design, an expression for old fashion assembling of a larger number of cassettes into a holder system with the typically square or rectangular plates operation typically in parallel. Also known as "filter presses" or "membrane plate filters" in the industry. A very common principle in the filtration industry and the design, column principle may be used for the present inventions bio-reactor.

The ceramic and metal based bio-reactor core is extremely tolerant around the cleaning issue. Sterilization may be performed with steam, high temperature exposure like 500 degree Celsius and exposure to warm fluid in the pH range of 1-14 pH. The bio-reactor core mounted in a housing manufactured from stainless steel or plastics suitable for fluid tights assessment and with mechanical strength for enclosure.

Sensor Integration

On-line measuring of $O_2$, pH, temp, $CO_2$, glucose, flow, pressures, etc. for understanding and process control is mandatory for optimum metabolism in the bio-reactor. Any of the inventions variations may include passageways incorporated for correspondence with traditional electrochemical 12 millimeter diameter sensors, probes for monitoring. Sensors as supplied from Hamilton, Mettler, etc. with Pg13.5 thread are used in the industry and inserted in ports via sealed connections being twisted open during insertion.

Though is preferable to use single-use sensors as to the fact that the industry shift to disposable bio-reactors bags, the need for disposable sensors also becomes important and a significant improvement. The above described bio-reactor cores arranged in a bag of flexible materials or in cassettes, capsules or the like from non flexible materials allow the bio-reactor to be single-use and disposable. It is advantageous to avoid introduction of any foreign articles such as standard electrochemical 12 millimeter diameter sensors, probes, transmitters after bio-reactor sterilization. And such sensors will not accept the sterilization or they loose their calibration. Relevant real-time sensors are such as for measurements of gases, dissolved gases, liquids, temperature, cell density, organics, pressures, etc.

The present invention in one embodiment do benefit from disposable sensors being integrated into the bio-reactor bag or capsule. Optical sensors have the advantages that they can be engineered to be non-invasive or introduced into the bio-reactor before gamma sterilization occurs, generally do not have stringent grounding requirements, and can often provide enhanced performance over existing chemical or electrochemical methods. A variety of sensors principles are used; chemical-optical, optical, fluorescence, near infrared spectroscopic—NIR, Partial Least Squares—PLS, Principal Component Analysis—PCS, radio frequency impedance.

Compact single-use sensors are manufactured by the German company PreSens Precision Sensing GmbH being flat to less than 1-5 millimeters, less than 50 millimeter in diameter with wires or electrical connectors extending from the sensor. Or the sensor elements are attached to the Inside of bio-reactor corresponding through the translucent container material to a transmitter on the outside for non-invasive and non-destructive operation. An alternative product is from Finesse Corp from USA who offers a line of disposable optical sensors for detection of dissolved oxygen and pH.

Operation Modes

Opposite of the common standard batch fermentation the present invention by far takes advantages of continues fermentation for cell growth followed by the actual expression from the micro organism. Batch fermentation reactor size vary from bench-top to 25 $m^3$ tanks, operate for 7-30 days and collection of cells or harvest takes place only once per fermenter cycle. Foaming as to the mixer operation in traditional batch operation with a head space is a problem in specific if oxygen take-up is done through the fluid surface in the reactor. In general the cell density is low and CIP, Cleaning In Place after operation is highly costly and documentation heavy. Flow speed, flux of the media passing the matrix, and perpendicular to the matrix should be in the range of 0.1-2,000 centimeter/hour/cm$^2$ preferably 10-150 centimeter/hour/cm$^2$.

Perfusion mode operation allow for continues expression and hereby constant harvest. The bio-reactor is operated in a configuration with one inlet and at least one outlet. The majority of the fluid flow volume is passing the matrix and re-circulated in orbital motion around the centre. A minor flow is taken out continuously including the product and processed separately. A similar volume is added as fresh nutrient including oxygen and other gas additions. As no head space is needed and the oxygenation is done outside the typical reactor foaming is not a problem.

Cross-flow (or tangential-flow) operation gets its name because the majority of the feed flow travels axially along the matrix core centre, rather than perpendicular across the matrix. The reactor feed fluid flow volume is significant larger than in pure perfusion mode. The technology offer continues expression and constant harvest as the advantage. In cross-flow mode the bio-reactor is operated in a configuration with one inlet and two fully independent and separated outlets. The feed flow volume to the reactor is the combined retentate (fresh nutrient passed the reactor un-used) and the permeate (used nutrient including product) flow. The advantage is unlimited individual adjustments of the three flows, which controls accurately:

1. the feed flow through the matrix (containing the micro organism) and
2. the reactor operating pressure and
3. equally important the retentate flow of fresh nutrient all along the inlet volume in the bio-reactor eliminating gradients Factors, which insures that any individual porous matrix bodies receive equal nutrient flow for elimination of gradients in each individual porous matrix cores. Cross-flow operation also allows precise control of the fluid shear forced in order to avoid removal of adhered cells from matrix surfaces. As no head space is needed and dissolved oxygenation is selected (no bubbles or sparging) outside the reactor the foaming problem is eliminated.

Human Made Semi Synthetic in-Organic Powder Materials

An alternative material for rigid matrix bodies (either for use as bioreactor or separation reactors) is by copying the human and animal material bone which consists of a biopolymer matrix (collagen) reinforced with mineral nano particles (carbonated hydroxylapatite), forming a natural composite which builds up a dense shell on the exterior and a network of struts with a mean diameter ranging 200 μm in the core of many bones. Bio ceramic hydroxylapatite (naturally occurring white mineral, calcium apatite (CaOH) with the formula $Ca_5(PO_4)_3(OH)$) and calcium phosphate containing bodies are known for promoting cell growth and being bio friendly. Used for more than a decade in dentistry and reconstructive surgery in the bio medical industry it is well known that hydroxylapatite based foams are highly suitable as matrix for cell growth. There are several approaches; such as rapid prototyping methods, ceramic gel casting and sintering to produce cellular structures with designed architecture from hydroxylapatite and other bio ceramics.

One way of manufacturing ceramic rigid large size carrier bodies is obtained by sintering a powder mixture comprising coarse-grain material and a fine-grain substance melting at a lower-than-sintering temperature gluing the coarse grains together in the contacts points. Produced from the bi-modal grain principle (coarse SIC grain F150 powders (~82 μm size) according to FEPA standards mixed with fine micro grained SiC FCP-15 (less than 1 μm size) both from French company Saint Gobain. The carrier with packed particles will have the surface area of app 20 m$^2$/kilo grain. And for Ø144×L152 millimeter–2.4 liter body at total 4 kilo×20 m$^2$/kilo=~80 m$^2$ internal surface area. For the comparison a 20 liters body will hold 20×2.4 kilo/liter×20=960 m$^2$ surface area. Such bodies are though not disposable but will handle sterilization unlimited as to their chemical inertness. Silicon Carbide and Mullite has compared to Alumina, Zirconia and Titania the advantage to accept manufacturing in larger diameters and lengths.

An alternative material for rigid matrix bodies is by copying the human and animal material bone which consists of a biopolymer matrix (collagen) reinforced with mineral nano particles (carbonated hydroxylapatite), forming a natural composite which builds up a dense shell on the exterior and a network of struts with a mean diameter ranging 200 μm in the core of many bones. Bio ceramic hydroxylapatite (naturally occurring white mineral, calcium apatite (CaOH) with the formula $Ca_5(PO_4)_3(OH)$) and calcium phosphate containing bodies are known for promoting cell growth and being bio friendly. Used for more than a decade in dentistry and reconstructive surgery in the bio medical industry it is well known that hydroxylapatite based foams are highly suitable as matrix for cell growth. There are several approaches; such as rapid prototyping methods, ceramic gel casting and sintering to produce cellular structures with designed architecture from hydroxylapatite and other bio ceramics.

Fibres in General

Any fibre from natural or artificial origin, which is capable, by itself or through further treatment, of adhering micro organisms on its surface, may be utilized. The material should be defined by several criteria:

1. tensile strength for processing the fibres into a 3D matrix structure
2. essentially insoluble in a neutral aqueous solution within a reasonable time
3. no release of substances, extractable into the aqueous media
4. bio compatibility with relevance to the specific micro organism
5. surface properties by nature or by treatment suitable for micro organism attachment Fibres may take shapes different from being round and solid, such as star shaped, square, octagon, triangular, hollow and their combinations.

Human Made Metal Fibres

Metal fibre with thickness of 1-50 μm are further suitable as raw materials for the here presented invention, design and manufacturing methods. Either drawn fibres or fibres cut or planed from solid materials into fibres such as the product Bekipor or Bekinox available from the Belgium company Bekaert. Typically the fibres are alloyed from at least elements like; ferrum, chromium, nickel, aluminium and preferably small parts of rare earth elements. Other selections from the elements and alloys may serve the task of attracting the micro organism. If matrix is fabricated from metal fibres then porosity range from 50% and could be higher than 90%.

Human Made Synthetic Organic Fibres

Synthetic fibres are the result of extensive research by scientists to improve upon naturally occurring animal and plant fibres. In general, synthetic fibres are created by forcing, usually through extrusion, fibre forming materials through holes (called spinnerets) into the air, forming a thread. Before synthetic fibres were developed, artificially manufactured fibres were made from cellulose, which originates from plants. Polyester is a category of polymers which contain the ester functional group in their main chain. Although there are many types of polyester, the term "polyester" as a specific material most commonly refers to polyethylene terephthalate (PET). Polyesters include naturally-occurring chemicals, such as in the cutin of plant cuticles, as well as synthetics such as polycarbonate and polybutyrate. Polyester is like all artificial crude oil based fibre materials hydrophobic, but the least hydrophobic and with less hydrophilic alike behaviour compared to than polypropylene. Biodegradable (aliphatic) polyester fibers (bio plastics) generated from agro resources sees increasing interest and may be the future for the disposable bio-reactors, such as polylactic acid and polyhydroxyalkanoates.

Polyester is a category of polymers which contain the ester functional group in their main chain. Although there are many types of polyester, the term "polyester" as a specific material most commonly refers to polyethylene terephthalate (PET). Polyesters include naturally-occurring chemicals, such as in the cutin of plant cuticles, as well as synthetics such as polycarbonate and polybutyrate. Polyester is like all artificial crude oil based fibre materials hydrophobic, but the least hydrophobic and with less hydrophilic alike behaviour compared to than polypropylene. The basic product is melt blown fibres or yarn cut into desired length and with thousand of needles from each side of a belt of fibres machining the fibres into a fabric called non-woven.

Biodegradable (aliphatic) polyester fibers (bio plastics) generated from agro resources sees increasing interest and may be the future for the disposable bio-reactors, such as polylactic acid and polyhydroxyalkanoates.

Organic, Vegetable Natural Grown Biological Fibres

Vegetable fibres are generally comprised mainly of cellulose: examples include cotton, jute, flax, ramie, sisal, coconut and hemp. Cellulose comes in several variations and the fibres serve world wide in the manufacture of paper and cloth. Cellulose in general offer hydrophilic behaviour and the fibres may be further categorized into the following:

Seed fibre: Fibres collected from seeds or seed cases. e.g. cotton and kapok

Leaf fibre: Fibres collected from leaves, e.g. sisal and agave.

Bast fibre or skin fibre: Fibres are collected from the skin or bast surrounding the stem of their respective plant. These fibres have higher tensile strength than other fibres. Therefore, these fibres are used for durable yarn, fabric, packaging, and paper. Some examples are flax, jute, kenaf, industrial hemp, ramie, rattan, soybean fibre, and even vine fibres and banana fibres.

Fibre: Fibres are collected from the fruit of the plant, e.g. coconut (coir) fibre.

Stalk fibre: Fibres are actually the stalks of the plant. E.g. straws of wheat, rice, barley, and other crops including bamboo and grass. Cellulose from trees, wood is also such a fibre.

The most used natural fibres are cotton, flax and hemp, although sisal, jute, kenaf, and coconut are also widely used. Hemp fibres are mainly used for ropes and aerofoils because of their high suppleness and resistance within an aggressive environment. Hemp fibres are, for example, currently used as a seal within the heating and sanitary industries and as part of composites for the automobile industry.

The use of cellulose materials as supports for immobilization of small molecules, proteins, and cells has received considerable attention for many years and possible applications have been pursued extensively. Chemically, cellulose is composed of β-D-glucopyranosyl units linked by (1→4) bonds and with additional inter chain interaction through hydrogen bonds, some of which form the so-called elementary fibrils. Elementary fibrils contain highly ordered crystalline regions and more accessible amorphous regions of a low degree of order. Cellulose is available in many different physical forms, such as fibres, micro granules, micro crystals, beads, gel particles, capsules, and membranes. Less pure cellulosic materials are used in industrial processes in the form of ropes, pulps, chippings, cloths, and paper.

Flax (also known as common flax or linseed) (binomial name: *Linum usitatissimum*) is a member of the genus *Linum* in the family Linaceae. It is native to the region extending from the eastern Mediterranean to India and was probably first domesticated in the Fertile Crescent. This is called as Jawas/Javas or Alashi in Marathi. Flax was extensively cultivated in ancient Egypt. Flax fibre is extracted from the bast or skin of the stem of the flax plant. Flax fibre is soft, lustrous and flexible. It is stronger than cotton fibre but less elastic. The best grades are used for linen fabrics such as damasks, lace and sheeting. Coarser grades are used for the manufacturing of twine and rope. Flax fibre is also a raw material for the high-quality paper industry for the use of printed banknotes and rolling paper for cigarettes. Fibres are often 20-50 millimeter long and 5-25 µm in diameter.

Hemp is the common name for plants of the entire genus *Cannabis*, although the term is often used to refer only to *Cannabis* strains cultivated for industrial (non-drug) use. The use of hemp for fibre production has declined sharply over the last two centuries, but before the industrial revolution, hemp was a popular fibre because it is strong and grows quickly; it produces 250% more fibre than cotton and 600% more fibre than flax when grown on the same land. In general the thickness of the fibres is on the high side ranging 50-400 µm and very long like half a meter. Hemp is one of the strongest natural fibres today. Widely misunderstood and undervalued for its usefulness, industrial hemp fibre has inherent insulating properties that wick moisture and helps block UVA and UVB rays. As a crop, it is naturally resistant to pests and therefore does not require heavy use of toxic pest and herbicides. As a fabric, like bamboo, hemp has natural antibacterial and anti-mold properties and happens to use a fraction of the water that cotton requires to grow. When it comes to growing, hemp is similar to linen, another stalk fibre.

Cotton is a soft, staple fibre that grows in a form known as a boll around the seeds of the cotton plant (*Gossypium* sp.), a shrub native to tropical and subtropical regions around the world, including the Americas, India and Africa. The fibre most often is spun into yarn or thread and used to make a soft, breathable textile, which is the most widely used natural-fibre in woven clothing today. Fibres are 91% cellulose, typically 12-20 micrometers in diameters and length varies from 10 to 60 millimeter. Cotton is also available as non-woven materials.

Viscose rayon is a man-made regenerated cellulosic fibre typical less than 10 µm in diameter and in any length before being chopped. Because it is produced from naturally occurring polymers, it is neither a truly synthetic fibre nor a natural fibre; it is a semi-synthetic fibre. Rayon is known by the names viscose rayon and art silk in the textile industry. It usually has a high lustre quality giving it a bright shine. Rayon contains the chemical elements carbon, hydrogen, and oxygen.

Organic, Animal Natural Fibres

Wool is a fibrous protein derived from the specialized skin cells called follicles. The wool is taken from animals in the Caprinae family, principally sheep, but the hair of certain species of other mammals including: goats, lamas, and rabbits may also be called wool. Wool has several qualities that distinguish it from hair or fur: it is crimped, it has a different texture or handle, it is elastic, and it grows in staples. Wool has been known for centuries in a non-woven format fabric. Wool fibres are hygroscopic (highly hydrophilic), meaning they readily absorb and give off moisture. Wool can absorb moisture almost one-third of its own weight. Fibre thickness varies between 15-80 μm depending on type of sheep where Merion sheep express fibres 15-25 μm thick. Length ranging mostly from 50-150 millimeter with a few sheep's able to express 300 millimeter long fibres. Wool is also available as non-woven, carded, wet laid method of manufacturing materials.

Silk is a protein based triangular prism alike fibre hand-made by the *Bombyx mori* worms kept in captivity. Cross section of the fibre is typically 5-10 μm though some fibres may reach 65 μm and most often available as woven material.

The present invention will take advantage of matrix in any thickness and design based on non-woven needle punched, rubbed, carded, wet laid method of manufacturing or woven fibres or packed by single fibres or a mix among the different fibres or any combinations hereof.

Surface properties such as the Zeta potential defines the electrical charge on particles and surfaces, or charge at the double layer surrounding the particles, in aqueous suspension and may be measured with a Zeta potential meter by means of known electro-foresis or flow of sedimentation potential measurements. Depending on the suspended particle surface properties, aqueous suspensions of particles exhibit a correlation between the pH-value of the aqueous suspension and the Zeta potential in the way that low pH-values establishes positive zeta potentials (hydrophobic alike) and high pH-values negative zeta potentials (hydrophilic alike). Between these extremes, most particles and surfaces have a so-called isoelectric point, where the zeta potential is zero and the particles are no longer repelled from each other by the surface charge and therefore flocculate due to van der Vaals forces. Not only at the isoelectric point, but also at a given range from this point, often at zeta potentials less than +−20 mV, suspensions tend to be unstable and partially flocculated. Very strong attachment may be achieved by mixing particles with opposite signs, +−, and high zeta potentials. As an example, if an immobile surface of a support material exhibits a high positive zeta potential (charge) at a certain pH-value, suspended particles will either stick to this surface if their zeta potential is negative or be repelled from the surface if their zeta potential is positive, and this behaviour may or may not be sensitive to pH-variations of the suspension. So, before designing the surface of a support material it is important to know the zeta potential profile of the components in the suspension in question.

The isoelectric points are in general difficult to measure precisely, cf. table 1, which is due to both the fact that the response at the isoelectric point for most analytical techniques is very weak because of the weak electrical forces and that the impurity level of the surfaces is not always well defined. But in spite of the scatter, tabulated values are still valuable in the design of surface properties, so if for instance the suspension has a positive zeta potential at neutral pH-values silica-surface is a poor choice whereas alumina, titania (anastase) or magnesia may be a good choice.

The inventive step in this context is therefore to measure the zeta potential of the suspension or solution, which is going to be in contact with the substrate material and thereafter establish a proper coating, if necessary on the substrate in order to adhere the particles or micro organisms to the surface during growth. Recycling or cleaning of the matrix surface is then performed either by changing the pH-value of the suspension or by applying a suitable voltage on the surface while cleaning the substrate.

TABLE 1 the pH of isoelectric point at 25° C.
for selected materials in water are:

| Metal oxides | Formula | Isoelectric point at pH | Reference |
|---|---|---|---|
| Vanadium oxide | $V_2O_5$ | 1-2 | 3 |
| Silicon oxide (silica) | $SiO_2$ | 1.7-3.3 | 2 |
| Silicon carbide | SiC | 2-3.5 | 2 |
| Zirconium oxide (zirconia) | $ZrO_2$ | 4 (−11) | 2 |
| Manganese oxide | $MnO_2$ | 4-5 | 2 |
| Titanium oxide (Rutile) | $TiO_2$ | 3.9 | 2 |
| Titanium oxide (Anastase) | $TiO_2$ | 8.2 | 2 |
| Silicon nitride | $Si_3N_4$ | 6-7 | 1 |
| Iron oxide (Magnetite) | $Fe_3O_4$ | 6.5-6.8 | 2 |
| Iron oxide (Maghemite) | $Fe_2O_3$ | 3.3-6.7 | 2 |
| Iron oxide (Hematite) | $Fe_2O_3$ | 8.4-8.5 | 2 |
| Cerium oxide (ceria) | $CeO_2$ | 6.7-8.6 | 2 |
| Chromium oxide (Chromia) | $Cr_2O_3$ | 6.2-8.1 | 2 |
| Aluminium oxide (Alumina) | $Al_2O_3$ | 7-8 | 1 |
| Yttrium oxide (Yttria) | $Y_2O_3$ | 7.2-9 | 2 |
| Copper oxide | CuO | 9.5 | 2 |
| Lanthanum oxide | $La_2O_3$ | 10 | 1 |
| Nickel oxide | NiO | 10-11 | 4 |
| Magnesium oxide (Magnesia) | $MgO_2$ | 12-13 | 2 |
| Glass | | 2.1 | 5 |
| PP, PET, HDPE, PVC | | 3.5-4 | 5 |
| Polyester | | 3-4 | 6 |
| Gelatine | | 4.9-9.4 | |
| Borosilicate glass | | <7 | 6 |

1. Brunelle JP (1978). 'Preparation of Catalysts by Metallic Complex Adsorption on Mineral Oxides'. Pure and Applied Chemistry vol. 50, pp. 1211-1229.
2. Marek Kosmulski, "Chemical Properties of Material Surfaces", Marcel Dekker, 2001.
3. Jolivet J. P., *Metal Oxide Chemistry and Synthesis. From Solution to Solid State*, John Wiley & Sons Ltd. 2000, ISBN 0-471-97056-5
4. Lewis, JA (2000). 'Colloidal Processing of Ceramics', *Journal of the American Ceramic Society* vol. 83, no. 10, pp. 2341-2359.
5. Fernando Soares Lameiras (2008) "Measurement of the zeta potential of planar surfaces with a rotating disk", Mat. Res. vol. 11 no. 2 São Carlos April/June 2008
6. Lieng-Huang Lee (1991) "Fundamentals of Adhesion"

Every surface of a material has a tendency to adsorb electric charges. The electrical state of a surface depends on the spatial distribution of free charges in its neighbourhood. The Zeta potential is a very important factor for the attraction of micro organism to the offered surface inside the porous matrix. Via selection of the correct materials it is possible to design the surfaces to be more or less micro organism adhesion friendly. If the base carrier materials are selected from a material type not really suited for anchoring the micro organisms, then an ultra thin surface coating with more suitable materials is one way of designing the surface properties according to the needs. One example being that a re-crystallized Silicon Carbide grain based wall-flow carrier with relative low Zeta potential may be modified via a surface coating with a Zeta potential more suitable by an ultra thin $TiO_2$ or Zeolite coverage. Such coating thickness ranging from a few nano meters to a few microns.

Typically Zeta potential range for micro organism culture support should be between 7.2 to 7.4 for mammalian micro organism (like CHO) culture, 6.2 to 6.4 for Sf-9 insect cells, and 6.4 to 6.5 for Hi-5 cells. And in general pH gradient should be reduced or eliminated being a feature of the present invention. According to the selected micro organisms surface properties determined by hydrophilic or hydrophobic actions must be taken into account. And different surface properties within the same container should be selected careful. Polyester fibres are typically less hydrophobic or become easier wetted, more hydrophilic so to speak, compared to the more hydrophobic materials like polypropylene.

Surface coating, of fibre surfaces, grain surface, membranes surfaces and matrix surfaces with Extra Cellular Matrices (ECM) promotes micro organism, cell attachment by stronger electrostatic attraction. Such absorbent as organic matters like peptides, proteins, amino acids, such as the artificial molecule poly-L-lysine or the protein product Matrigel, Collagen, Fibronectin, Laminin or 1% gelatine suspension as coating supporting becoming more hydrophilic for the micro organisms to anchor faster, give higher level of affinity.

The cells attachment to the non-woven polyester based matrix will benefit from pre-treatment passing through a plasma torch, corona field and further washed with methanol. Potentially sterilized under a UV light and then immersed in a solution of 100 μg/mL poly-D-lysine and finally rinsed with sterile water.

Some Biomimetic materials offer even stronger electrostatic attraction than the amino acids (like poly-L-lysine) such as the laminin family containing the protein domain isoleucine-lysine-valine-alanine-valine (IKVAV).

The examination of growth surfaces for adhesive mammalian cells is a large scientific discipline. Usually, manufacturers use inexpensive materials like synthetic polymers or glasses, which easily can be formed in different structures in large quantities. Synthetic polymers are, however, usually hydrophobic, and cells prefer to attach to polar or charged surfaces. Therefore, surface treatment of the polymer by radiation or coating by hydrophilic compounds or nano coatings has been used in different context. The optimal surface will depend on the cells and their use. Although biomimetic technology and nano technology is in its infancy, with no applications yet reaching commercialisation, the barriers in some cases lie mainly in scaling up production processes to industrial levels.

Coating of fibre surfaces does have other purposes like anchoring the fibres to each other in order to increase stiffness, mechanical strength of the felt. Such a binder in solutions could be resins, epoxy, melamine, polyvinyl alcohol, polyvinyl acetate or the like. Surface coating may also be impregnation with absorbent powders such as activated carbon, pyrolytic carbon, diatomaceous earth, perlite cay or such. Similar or other materials, molecules embedded in the matrix carrying a positive (cationic) electro kinetic charge and chemically bonded to the matrix will further improve also the mechanical strength. Since most micro organism and contaminants found in the media are negatively charged (anionic), they will be inherently attracted to the positive charged matrix.

Surface treatment of the matrix for increased surface energy may preferably be performed by glow discharge treatment such as gas plasma treatment, corona treatment in order to elevate the surface-free energy. Its though quite complex mechanism as high surface-free energy cannot be correlated unambiguously with excellent hydrophilic properties (ref to Robert E. Baier & Anne E. Meyers article "Aspect of Bioadhesion", 1991). Artificial electrostatically charging the matrix are possible after assembling when based on specific materials being somewhat electrical conductive, such as metal or few ceramics and specialty plastics. Electrostatically charging allows suspension cells such as hybridoma to adhere easier to the surface and become trapped in the matrix where they, depending on shear forced, remain throughout the process. The electrostatic charge is similar to the binding charge to which plastic tissue culture ware is exposed. Electrostatically charging of materials like polyester is done to some extent by washing the polyester material in ethanol or methanol.

Media Composition

Today, there is a multitude of different nutrient compositions for specific cell or micro organism types. Basically they are all based on:

Carbon source and/or energy source
Organic nitrogen source
Minerals
Vitamins

Glucose concentration should not fall below 1.0-1.5 g/L with initial glucose concentration of >3.5 g/L). $CO_2$ concentration is an important factor for adjusting the pH level with ratio to $O_2\tilde{\ }1:5$ and tension of $CO_2$ ranging 1-10%.

Oxygen Supply Considerations

In an aerobic process, optimal oxygen transfer is perhaps the most difficult task to accomplish. Oxygen is poorly soluble in water, even less in fermentation or bio-reactors reactors. Oxygen content in the nutrient is highly important and cells like CHO constantly need 0.31 pmol/cell/h. As Oxygen is poorly dissolved in water $O^2$ access often becomes the limiting factor for cell growth and protein expression. Oxygen transfer is usually helped by sparging (gas bubble flushing) and agitation, which is also needed to mix nutrients and to keep the fermentation homogeneous in stirred tanks. There are, however, limits to the speed of agitation, due both to high power consumption (which is proportional to the cube of the speed of the electric motor) and to the damage to organisms caused by excessive impellor tip speed in traditional suspension vessels or bags.

Another attractive method is the use of the "oxygenator", which is a medical device capable of exchanging oxygen and carbon dioxide in the blood of human patient in surgical procedures that may necessitate the interruption or cessation of blood flow in the body, a critical organ or great blood vessel. It's a disposable device and contains about 2-4 $m^2$ of a membrane permeable to gas but impermeable to fluids, in the form of hollow fibre module.

Combined in the bio-reactor external fluid circuit, the oxygenator is located outside the bio reactor as a separate reactor to which the nutrient pass through before being entered to the bio reactor. The oxygenator sees on the other side of the membrane either air, oxygen or a controlled gas composition in order to control the dissolved gases in the media.

Seeding Consideration

Nutrient velocity dynamics and flow profile though the matrix have huge impact on the spontaneous deposits of the micro organism prior to colonization. Relative strength of adhesion are related to initial surface tension of the matrix surface and reflects the integrity of the first conditioning films, which is usually dominated by proteins. Fluid flow effects, such as shear stresses also play a critical role in the process of inoculation.

Expression Considerations

Current expression rates by adhering mammalian cells depend upon the type of molecule to be produced and the basic rule is that high surface area enables high cell yields. And in general present day technologies are faced with the fact that the cell density drop from $2-5\times10^{*8}$ cell/mL on the best 500 mL bench-top bio-reactors with a factor 100 to maximum industrial volume stirred tank.

Based on common available reference the following general data for is obtained from relevant available commercial data, advertising, articles:

Bench-top batch operation in very small scale on CHO cells:
  The BelloCell/FibraStage 500 mL volume bottles can offer cell density of $2\times10^{*8}$ cells/mL.
  T-flasks or roller bottles can offer cell density of $1\times10^{*7}$ cells/mL.
  Replace media regularly.

Bench-top batch mode operation on CHO cells in 1-15 liter volume:

The CelliGen with 50 gram FibraCell fibre discs can offer cell density of $1\times10^{*8}$ cells/mL.

The FiberCell hollow fibre can offer cell density of $1\times10^{*10}$ cells/mL.

Stirred vessel suspension system can offer cell density of $1\text{-}10\times10^{*6}$ cells/mL.

Opt'Cell ceramic carrier, perfusion mode, could offer cell density of $1\text{-}2\times10^{*6}$ cells/mL.

Replace media regularly.

Pilot scale batch operation 15-100 l volume on CHO cells:
Fluidised bed with micro carriers can offer cell density of $1\times10^{*8}$ cells/mL.

Stirred tank suspension system can offer cell density of $5\times10^{*7}$ cells/mL.

Wave bag suspension system can offer cell density of $1\text{-}10\times10^{*6}$ cells/mL.

Industrial scale operating 100-250 liter volume on CHO cells:
Fluidised bed with micro carriers can offer cell density of $1\times10^{*7}$ cells/mL.

Stirred tank can offer cell density of $5\text{-}10\times10^{*6}$ cells/mL.

Perfusion system can offer cell density of $1.5\times10^{*8\text{-}6}$ cells/mL.

Production values, data was somewhat more difficult to obtain:
T-flask, less than half liter medium, $2\times10^{*9}$/mL cells, express 1.5 mg/L/day Bench-top—Celline CL1000, stirred, suspension, $1\times10^{*7}$ cells/mL, express 25-50 mg/L/day Pilot scale—Wave bag produce 10-50 mg/L/day Pilot scale—stirred, batch, $1\times10^{*7}$/mL cells, express up to 200 mg/L/day Bench-top—CelliGen, FibraCell fibre discs, 1 liter volume, express up to 500 mg/L/day Productivity/titer per liter reactor volume, CHO cells for antibody production.

Alternatively its possible to express the volumetric productivity in picograms per cell per day. In 1986 the industry standard was 10 pg/cell/day for CHO cells. By 2006 the absolute highest product titer has ten fold increased to 100 pg/cell/day equivalent to 500-1,000 mg/l/day. Though its more realistic to expect 20-60 pg/cell/day expression capacity for CHO cells. All off the above are not achieved by increasing cell density, but entirely by optimised cell performance through better nutrient and conditions. Even with cell culture density of $1\times10^{*7}$/mL cells the total biomass represent less than 5% of the culture volume and leaves plenty room for the here presented invention.

EXAMPLES

Example 1

Documented Performance

Reference is made to the work of Guozheng Wang, et. al documented in the article "Modified GelliGen packed bed bio-reactor for hybridoma cell cultures" Cytotechnology 9, page 41-49, 1992. Two test were performed on the New Brunswick Scientific product named CelliGen 2.5 liter reactor.

1. a packed-bed column system packed with 50 gram FibraCel carriers (500 mL volume) in perfusion mode with 200 mL/min external pump controlled nutrient flow and $\sim 1\times10^{*8}$/mL cells with expression of 0.5 g/L/day MAbs.

2. a packed-bed basket system packed with 110 gram FibraCel carriers (1,000 mL volume) with 3,000 mL/day nutrient flow with internal perfusion circulation pump and $\sim 1\times10^{*8}$/mL cells with expression of 0.5 gram/L/day MAbs.

Examples 2

Polyester Fibre Discs

For the present invention, in a mass production scale, in a polyester disc stacked body the nutrients, fresh media to the CHO micro organisms is introduced internally and pumped through the reactor constantly to the circumference drainage of the reactor. FIG. 1 illustrates how the discs are oriented with central feed inlet and circumference drainage outlet for even mass flow though each $cm^3$ of the sheets. As the fibre based discs is able to support $1\times10^{*8}$/mL CHO cells, then:

In a 70 liter container the present invention offer $4\times10^{*4}$ $cm^3$ of porous matrix volume in the stacked sheets based on non-woven fibre felt sheets Documentation from individual sources show that conservatively $1\times10^{*8}$/mL CHO cells are able to produce 500 mg/L/day proteins, when anchored on randomly oriented polyester fibre bodies (FibraCell)

In 1 $cm^3$ porous substrate of this invention the cells then under best conditions express 500 mg/mL/day protein Multiplying the volume and production rate gives this excellent figure of 40 liter×500 mg/L/day=20 gram/day Example 3

Non-Woven Matrix

A fermenter assembly and method as depicted in FIG. 12 was tested at Aarhus University in Denmark with hybridoma cell line 9E10 (ATCC#CRL-1729). The overall reactor 121a consisted of a single compartment in which non-woven polyester matrix sheets (pore size 25-50 μm, product FITEVIG 353 M25, supplied by company Fibertex in Denmark). The disc diameter was 80 millimeter and the total volume of the matrix 121 was approximately 226 $cm^3$ and the medium volume 500 $cm^3$. An external medium loop with a flow rate of 100 mL/min drew from the bottom of the reactor through an oxygenator (hollow fiber module UFP-3-C-4A, GE Healthcare) and a pump before medium entered the center of the matrix module again. The oxygenator 127 on the permeate side had a steady flow of 95% air/5% $CO_2$ to supply oxygen and control pH. The reactor dO, pH, temperature data were collected, harvest and feeding controlled with a BioStatB DCU unit (Sartorius) and custom-made data acquisition software (Foxylogic.com). Temperature was kept at 37° Celsius by emerging the reactor unit into a water bath of water.

To reduce the hydrophobicity and to increase the biocompatibility, the non-woven PE matrix discs were rinsed twice with 95% EtOH for 2 hours and then treated with 1% w/v NaOH for 1 hour at $\sim 100°$ C., followed by extensive rinsing with water. The matrix discs were then packed into the fermenter (4 disc pieces per stack in total 8 millimeter thick per stack; total of 6 stacks with flow-net spacers in-between similar to FIG. 1) and the reactor assembly rinsed with PBS-buffer. The reactor with installed dO (dissolved Oxygen), pH and temperature probes, external loop and oxygenator was then autoclaved. Following, the reactor was treated with 40 mL sterile PBS-buffer with 200 Units/mL Penicillin-Streptomycin with 5 mg poly-L-lysine to increase the biocompatibility, enough to fully wet the matrix. The mixture was left to rest for 5 min, and then supplemented with 750 mL PBS-buffer with 200 Units/mL Penicillin-Streptomycin. Buffers were pumped into the fermenter via the feed using the pumps on the BioStat-B DCU unit. The circulation pump was started and left for 30 min to rinse tubes and reactor. Air trapped in the matrix stack was driven out through 126. The bio-reactor was then drained via both the feed and farvest lines using the pumps on the BioStat-B DCU unit, and rinsed with 500 mL sterile PBS-buffer with 200 Units/mL Penicillin-Streptomycin followed by a rinse with 500 mL CD Hybridoma Complete medium (CD Hybridoma Medium, 8 mM (milliMole) Glutamine, 100 Units/mL P/S) was pumped into the fermenter via the feed line 125c and circulated for 10 min, then drained. The matrix retained volume was measured to ~50 mL. Finally, the fermenter was filled with CD Hybridoma Complete. It was visually inspected that the fermenter was sealed correctly before water added to the water bath. The temperature stabilized at 37° C. after 1.5 hours. The dO probe was allowed to repolarise for 8 hours, then left for 2 hours without air supply to check that no infection was present.

The fermenter was seeded with 130 mL of seed culture of hybridoma cell line 9E10 (ATCC#CRL-1729) with a total of $4.0 \times 10^8$ cells, viability >95%, were added to the fermenter through the seed line with a flow of 6 mL/min. The reactor flow was set to a flow of 200 mL/min (0.8 cm/min flux) for 1 hour to allow cell to move into the matrix before it was left for the rest of the experiment with at flow of 100 mL/min (0.4 cm/min flux). Seed density in the non-woven polyester matrix was calculated to ~$1.8 \times 10^6$ cells/mL matrix volumes.

For the following days the reactor was monitored for cell activity by tracking glucose consumption and antibody production. Glucose consumption was monitored using an enzymatic D-glucose kit (R-Biopharm GmbH) and antibody titer measured using capture on a Protein-G HP column on a HPLC system. Medium exchange was started at day 3 at a rate of 0.5 reactor volume/day with CD Hybridoma Complete with 4 mM Glutamine and maintained for 16 days.

Example 4

Ceramic Honeycombs

Test was performed at Rouen University in France on various porous ceramic parallel wall flow bodies all with sizes Ø25×L50 millimeter and with the Wall-Flow-Filter design. Fresh nutrients, media to the cells is introduced externally and pumped through the reactor constantly in perfusion mode. An outlet or slip stream after the reactor takes out similar volume as permeate containing the desired proteins and waste product. Outside the bio-reactor partial drainage passed through a separator to harvest the proteins. Hereby the nutrient purity inside the reactor is constant through the life of the cells. For the described bio-reactor the flow of media is in the range of 200 mL/m²/h at 37° Celsius and at pH 7.4 delivered at less than 10 kPa system pressures. As to the short reactors gradients was not a problem.

| Material Days after seeding | TiO2-200 cpsi Table 2 Glucose-g/L concentration | TiO2-200 cpsi Table 3 Lactate-g/L concentration | SiC-150 cpsi Table 4 Glucose-g/L concentration | SiC-150 cpsi Table 5 Lactate-g/L concentration |
|---|---|---|---|---|
| 0 | 4.4 | 0.1 | 4.5 | 1 |
| 5 | 4.4 | 0.4 | 4.6 | 1.5 |
| 10 | 4.3 | 0.5 | 4.0 | 1.8 |
| 15 | 4.3 | 0.6 | 3.5 | 3.5 |
| 20 | 4 | 0.7 | 3.5 | 5.5 |
| 25 | 3.8 | 1.1 | na | na |

Table 2 and table 3 good performances with 0.5 mm wall thickness, TiO2 WWF, 5 mL/h flow rate, no re-circulation where the cells adhered quite fast after introduction. Table 4 and table 5 show good cell growth with 0.8 mm wall thickness, SiC WWF design, 5 mL/h flow rate, no re-circulation, the cells needed a few days to adhere to the surface. Lactase concentration is increasing and glucose drops as a function of cell growth and expression.

The invented conical channel honeycomb bio-reactor calculation basics are:
  The body dimension Ø144×L152 millimeter of the wall flow bio-reactor with 0.5-5 cpsi (cells per square inch) type based on ceramic materials have the volume of 2.4 liter, bulk density of 2.2 being >4 kilo
  One kilo of ~90 μm size (Fepa standard F-150) ceramic grain, powder offer as much as 20 m²/kilo surface area
  One square meter of grain, powder surface is $1 \times 10^{*12}$ μm² theoretically leaving room for $25 \times 10^{*10}$ cells as the cells are app 15 μm in diameter when attached to the surface
  The invented bio-reactor will in a single body configuration offer the volume of 2.4 liters and the weight of app 4 kilo. Produced from the bi-modal grain principle the carrier will have the internal wall grain surface area of 4 kilo×20 m²/kilo=~80 m² internal surface area.
  One liter of bio reactor/20 m² are able to anchor $25 \times 10^{*10}$ cells=$5 \times 10^{*12}$ cells which express 2,000 mg/day product, then a 2.4 liter volume core produce 4,800 mg/day.

The conical channel honeycomb embodiment as seen in FIGS. 8 and 10 are when based on organic fibres an interesting low-cost alternative to high-tech man made materials such as ceramic powders.

Items of the Present Invention

The following section discloses aspects and embodiments of the present invention present in the form of items as cited herein below.

1. A bio-reactor apparatus for culturing immobilized cells, such as micro organisms, comprising a porous three-dimensional matrix, said matrix having a least two porous walls arranged in parallel or partly in parallel with a bio-reactor inlet separated from a bio-reactor outlet by said porous walls, wherein said bio-reactor inlet is capable of diverting feeding liquid to the matrix in a flow path having a first orientation, wherein said core, via hydronic forces, conveys fluids to pass each of the individual core matrix parts perpendicularly to said first orientation, wherein said matrix is suitable for anchoring and/or supporting the growth of living cells.

2. A modulus build bio-reactor device prepared according to item 1, where the individual porous bodie(s) of the core are fibre based sheets assembled around an inlet volume forming liquid distribution passages with an exhaust volume for liquid distribution passages and further arranged in such a way that the inlet volume are separated from the outlet volume by the sheets of porous material hereby creating a parallel structure.

3. A modulus build bio-reactor device prepared according to any of the previous items, wherein the core is assembled from discs structures suitable for stacking said discs being shaped to desired configuration such as round, square, rectangular or combinations hereof comprising an liquid distribution passage inlet volume with an exhaust liquid distribution passage volume and further arranged in such a way that the inlet volume are separated from the outlet volume by the sheets of porous material. The discs further stacked in such a way that said discs are assembled two-by-two creating a symmetrical arrangement with inlet volume in between each inlet set of discs corresponding with the common inlet and the outlet volume are isolated from the internal volume by the three-dimensional porous matrix which on the outlet side of the discs corresponding with a common outlet at the circumference.

4. A modulus build bio-reactor device prepared according to any of the previous items, where the porous matrix core are non-woven or woven fibre based sheets arranged pleated or stacked with inlet annular liquid distribution passages around a cylindrical inlet volume with an exhaust volume external to and surround the annular liquid distribution passages of the core and further arranged in such a way that the inlet volume are separated from the outlet volume by the sheets of porous material and the closed core ends hereby creating a parallel structure. Further being a plurality of longitudinal pleats, each of the pleats having a pair of legs, each of the legs having a first and a second surface, the pleats being in a laid-over state in which the first surface of one leg of one pleat is in intimate contact with the first surface of an adjoining leg of said one pleat and the second surface of said one leg is in intimate contact with the second surface of an adjoining leg of an adjacent pleat over substantially the entire height of each leg and over a continuous region extending for at least approximately 50% of the axial length of the bio-reactor device.

5. A bio-reactor device according to any of the previous items, wherein the configuration is of spiral design being circular assembling a number of matrix core envelopes sandwiches around drainage spaces and separated by feed spacers.

6. A modulus build bio-reactor device prepared according to any of the previous items, where the enclosure for porous bodies, grain, micro spheres or fibres are shaped by at least one stackable envelope of porous materials around a central inlet device, a circumference outlet hereby creating a radial channel system and ultra compact parallel structure such envelope material having porous walls.

7. A modulus build bio-reactor device prepared according to any of the previous items, where the individual porous body(s) of the core is a based on a porous organic foam matrix.

8. A bio-reactor device prepared according to any of the previous items, wherein the support is a honeycomb structure with a first plurality of blind separation cavities extending perpendicular into said body from said inlet side surface and a second plurality of blind separation cavities extending perpendicularly into said body from said outlet side surface, said blind separation cavities of said first and second pluralities being arranged spaced apart and mutually juxtaposed, the membrane bio-reactor device being composed of a number of longitudinal porous membrane bio-reactor device elements assembled so as to form said separation cavities, the method comprising transmitting the liquid into the first plurality of blind separation cavities and perpendicular through the porous walls into the second plurality of blind separation cavities.

9. A bio-reactor device prepared according to any of the previous items, wherein the support is a honeycomb structure with sets of circular blind separation cavities extending perpendicular into said body from said inlet side surface and a second set of plurality of blind circular separation cavities extending perpendicularly into said body from said outlet side surface.

10. A bio-reactor device according to any of the previous Items comprising:
 a) a membrane supporting three-dimensional porous matrix structure
 b) a porous membrane on the outlet, down stream side of the membrane supporting structure, said supporting structure having a nutrient inlet face, a membrane outlet face and a thickness or porous matrix in between said faces, said bio-reactor having in operation a biolayer on the three-dimensional porous wall matrix surfaces between the nutrient inlet and the outlet membrane; wherein the matrix allows diffusion of a nutrient solution from the nutrient face to sustain, feed the biolayer or micro organism allowing the biolayer product to pass through the porous matrix and the fine pored membrane (s).

11. A modulus build bio-reactor device prepared according to any of the previous items, wherein the core is a discs structure suitable for stacking and hereby creating a parallel structure. The stacked discs being shaped, cast, moulded to desired configuration. Said discs stacked in such a way that the discs are assembled two-by-two creating a symmetrical arrangement so the inlet space in between the disc corresponding with the common inlet for liquid distribution and the outlet are isolated from the internal volume with a membrane on the outlet side of the discs corresponding with a common outlet volume with liquid distribution passages at the circumference.

12. A bio-reactor device according to any of the previous items, where the reactor core is housed, enclosed in a container having:
 a) at least one inlet channel, hose, tube or flange for admitting the nutrient solution to the nutrient inlet face of the core structure and the nutrient re-circulation
 b) at least one outlet channel, hose, tube or flange for removing the product and the used nutrient solution from the three-dimensional porous matrix.
or any combinations of the above.

13. A bio-reactor device or parts of a bio-reactor device prepared according to any one of the items, wherein parts of the device are based on:
 a) Synthetic polymers in general, such as; resins, polycarbonate, polypropylene, polyethylene, polyethersulfone, polyester, polyoxyethylene, polyacrylonitrile, Polysulfone, ethylene vinyl acetate, polyvinyl acetate, cellulose acetate, polytetrafluoroethylene, aramide, Polychlorotrifluoroethylene, Polyfluoroethylenepropylene, polyvinylidene fluoride, polyvinylidene chloride, polystyrene, Polyamides, acetal, acrylics and further thermoplastics in general
 b) Synthetic elastomers, rubber in general, such as silicone, ethylene propylene rubber (EPM), ethylene propylene diene rubber (EPDM), Fluoroelastomers (Viton), neoprene, polyurethane, nitrite, butyl,
 c) Natural polymers (also bio polymers) in general, any form of fibres or particles, such as; rubber, latex, cellulose, cellulose variations, dextran, chitin, collagen, fibrin, keratin, starch, paper, cotton, wool, flax, hemp, coconut, jute, resins, viscose rayon, human and animal organic structures such as bone, tissue and further carbon and carbon element containing structures in general d) Synthetic bio degradable polyester (bio plastics) in general, like; aliphatic polyester such as polylactic acid polymers and polyhydroxyalkanoates families, polybutylene succinate, etc
e) Ceramics based on powders, grains and/or fibres, such as non-oxides and/or oxides and/or nitrides based on, SiC, Titanium, Aluminium, Silicon, Zirconium and their combinations
f) Human or animal bone or skeleton substitutes such as hydroxylapatite and/or calcium phosphate and/or carbonated calcium variants
g) Insects skeleton materials like chitin
h) Natural organic protein containing materials such as gollagen, gelatin and similar substances
i) Synthetic carbon fibre based substances
j) Metal powders and/or metal fibres and their combinations
k) Glass spheres, glass fibres, fibre glass
l) A binder being a glassy phases a resins or their combinations
m) Micro or macro carriers, macro beads, rasching bodies and polyester fibre porous discs less than 10 millimeter in diameter or porous micro carriers less than 5 millimeter in diameter or any combination hereof, like in any symmetric or asymmetric configuration, or any combination of materials in any shape combined.

14. A bio-reactor device according to any of the previous items, integrating at least one sensor, probe, transmitter collecting signals for a controlling device in order to obtain suitable conditions in the reactor core, the sensor designed such as;
   a) where the reactor core is enclosed in a container, bag, capsule, cassette integrating at least one sensor or probe for measurements of either of or all of; pH, dissolved oxygen, dissolved carbon dioxide, temperature, pressure and cell density, or
   b) where the reactor core is enclosed in a container, bag, capsule, cassette integrating at least one disposable, single-use sensor or probe for measurements of either of or all of; pH, dissolved oxygen, dissolved carbon dioxide, temperature, pressure and cell density
or any combinations of the above.

15. A bio-reactor device according to any of the previous items, integrating a temperature conditioning device with the purpose to keep a suitable temperature in the reactor core, such as;
   a) where the reactor core is housed, enclosed in a double circumference wall container, said circumference volume between the container walls housing a heating device or circulating a heating fluid for exchange of heat.
   b) or where the reactor core is housed, enclosed in capsule, cassette housing a temperature conditioning device.
   c) or where the reactor core matrix parts is laminated with a temperature conditioning device integrated within the fluid carrying spacers.
   d) or where the reactor core is housed in a vessel, container, bag which is surrounded by a flexible heating element on the out side.
or any combinations of the above.

16. A bio-reactor device according to any of the previous items or parts of a bio-reactor device prepared with adjustment of zeta potential to within the range of 2-7.5 pH generating a hydrophobic surface attraction, behaviour and micro organism friendly surface.

17. A bio-reactor device according to any of the previous items comprising an electrically conductive matrix or matrix supporting structure with electrical connections to the core in order to charge, change or modify the bio-reactor electrical potential for improved attraction of the biofilm, micro organism to the three-dimensional porous matrix.

18. A bio-reactor device according to any of the previous items, wherein the fibres, yarn, grains, spheres in the matrix is coated, covered with a surface treatment and/or a wash coat and/or a catalytically active coating and/or a nano particle coating obtaining a micro organism adhesion friendly surface or the opposite or combinations hereof.

19. A bio-reactor device according to any of the previous items, wherein the biofilm, surface layer of, agglomeration of micro organism comprising biological matter is selected from the group consisting of; bacteria, fungi, algae, plankton, animal cells, mammalian cells, tissue cells, yeast cells, plant cells, insect cells, protozoa cells, prokaryotic cells, eukaryotic cells, archaea cells or other biological matter.

20. A bio-reactor device according to any of the previous items, wherein the biofilm, surface layer of micro organism, agglomeration of micro organism express biological matter, such as; micro organism, cells, proteins, recombinant antibodies, enzymes, monoclonal antibodies, therapeutic antibodies or other biological matter.

21. A bio-reactor device according to any of the previous items having inlet channels for admitting the nutrient solution to the nutrient inlet face of the supporting structure, and outlet channels for removal of the used nutrient solution from the three-dimensional porous matrix of the supporting structure, and an external system for replacing the used nutrient solution with fresh.

22. A bio-reactor device according to any of the previous items incorporation a single-use pumping device for fluid transport within the bio-reactor and with external devices.

23. A device with design according to any previous items suitable for separation of particles from a fluid.

24. A method for industrial micro organism cultivation according to any of the previous items in a liquid using a bio-reactor device having numerous bio micro organisms located inside the porous matrix prohibited from passing the porous matrix by selective pore size of porous media. At least a part of the nutrient flow volume and the product outlet volume communicate only through the porous matrix wall hereby passing the micro organism.

DESCRIPTION TO THE DRAWINGS

FIG. 1—Illustration of one embodiment of the bio-reactor according to the present invention. A total of 20 matrix sections (11) stacked individually into a column and separated by feeding spacers (15a) and drainage spacers (15b) and contained in a bio-reactor having end wall sections (10a, 10b) and a circumferential wall section (19).

The principle of the invention incorporates a plurality of identical or differently shaped matrix sections, such as discs (11) arranged adjacent to each other and around a perforated feeding tube (10c) having a central inlet (12) and an outlet (13). The design eliminates gradients and gives an extraordinarily uniform flow distribution of nutrients through the reactor and a uniform distribution of biological cells.

The individual matrix sections (11) are stacked in sets adjacent to each other and separated on the inlet side by feeding spacers (15a) acting as radial fluid flow passage ways; the feed spacers (15a) are sealed (15c) which restrict any flow connection with the circumferential collection volume (13), thereby forcing the flow axially through the matrix sections (11). Drainage spacers (15b) on the outlet side of the stacked matrix sections (11) receive the axial feeding liquid once it has passed through the matrix (11). The drainage spacers are sealed (15d) so that feeding liquid cannot flow back into the inlet zone (12), but is instead diverted to the collection volume (13) located at the circumference of the bio-reactor. The drainage spacers (15b) are in liquid contact with radial extending outlet slots which divert feeding liquid from the exit side of the matrix sections (11) to the collection volume (13)—thereby guiding the feeding liquid and bioactive compounds produced to a top collection volume (16), thereby passing a set of stacked, flow net rings (17). The symmetrical arrangement ensures that the inlet (12) and the outlet (13) are isolated from each other by the matrix sections (11)—which matrix sections represent the only flow route for the feeding liquid through the bio-reactor.

The alternating feeding spacer sections and drainage spacer sections may be symmetrical and comprise or consist of different or identical layer(s) of flow net with an array of ribs arranged coaxially, thereby allowing feeding liquid and cells to pass unrestricted. Furthermore, the spacers may be of an asymmetrical design with coarser net(s) and screens laminated on each side with finer mesh flow net layers directly contacting the porous matrix sections. The finer flow net will eliminated the intrusion of fibres, particles, grains, spheres and the like from the matrix to penetrate into the spacer volume and restrict the flow of feeding liquid. The flow path through the porous matrix sections is axial for the shortest possible path way. In one embodiment, each of the 20 matrix sections holds 112 $cm^3$ in volume, the total matrix volume being 2,300 $cm^3$ in a body of Ø139×L244 millimeter matrix (disc) section.

FIG. 2—Illustration of one embodiment of the bio-reactor according to the present invention. Stacked matrix sections (discs) are separated by cast plastic parts creating a fully housed bio-reactor (24). A partly open view with a 90 degree cut away for clarity illustrates space for a plurality of identically shaped and stacked matrix sections (21) (3 matrix sections shown, 5 matrix sections removed) arranged along and around a central feeding tube (22)—thereby creating a cylindrical bio-reactor container.

The matrix sections (21) are surrounded by an outlet (23) arranged in the circumference of the bio-reactor as a collection area for 3 double drainage spacers (25b) and two, end-positioned, single drainage spacers (25c), one at the top and one at the bottom of the stacked matrices.

The view is for perfusion mode operation, but could be cross-flow with an extra fluid connection in the bottom cover opposite of (24a) the inlet volume (22). The rotational, symmetrical arrangement with four conical feed spacers (25a) equipped (with ribs on each side to separate symmetrical the two neighbouring discs (21)) corresponds with the common central inlet (22), but not with the common outlet (23) on the circumference, which is isolated from the inlet volume (22) by the matrix sections (21). The opposite conical design has been applied to the drainage spacers (25b) located in between 6 set of matrix sections (21). The drainage spacers are flow sealed at the centre and attached to an inner tube (25d) part facing towards the inlet (22), so the media flow freely towards the common outlet at the circumference around the core connected to the collection volume reservoir (23) encapsulating the bio-reactor core from top to bottom.

Both feed spacers (25a) and drainage spacers (25b, 25c) have on the circumferential side a short cylindrical part (24c) to ensure stable dimensions around the collection volume reservoir (23) outside the bio-reactor core and potentially a temperature conditioning device (not shown) in a tight fit around the bio-reactor (24). Said collection volume reservoir (23) corresponds with horizontal cavities (26) under top cover (27) of the bio-reactor core (24) and the only inlet (24a) and primary outlet (24d), as well as secondary outlet (24b) and corresponds with external pumps, valves, etc (not shown) for fluid control and general bio-reactor operation.

The entire set-up can be manufactured from disposable plastics, such as bio compatible plastics if desired and the purpose of introducing non flexible plastics as container materials is to create a single-use system easy to dispose of after use. The illustrated bio-reactor has a diameter of 142 millimeters, a height of 189 millimeters and contain 8 matrix sections each 180 $cm^3$ in total 1.5 liter volume.

FIG. 3—A 180 degree cut illustration of FIG. 2 connected with two diaphragm pumps, though the pumps are illustrated only in a simplified way. The bio-reactor (34) with space for 8 matrix sections (31) integrates symmetrically at each end a membrane pump (38a, 38b). Both membrane pumps (38a, 38b) offer an individual operation method as desired to be performed, though they are fluid interconnected through the matrix centre (32) and the circumferential collection reservoir (33). Both pump membranes (38c) is controlled from electronics (not shown) in housings (34a, 34b). Membrane (38c) in housing (38a) is fully expanded and membrane (38c) in house (38b) is not expanded. Valve fixation points (38d, 38e) (valves not shown) at each end of the fluid distribution centre (32) participate in the fluid direction control. External valves (not shown) at tubes (38f) and (38g) participate in the fluid control method. External gas pressure and electrical connection is illustrated passing a relevant number of tubes (38h). The invented combination of bio-reactor and pumps/method of operation eliminate the traditional need of external peristaltic pumps and achieve a simplified operation and lowered operation costs from single-use product.

The two identical pumps and membranes (38c) housed in pumping sections (38a, 38b) can be disposable and—at production set-up—can be supplied fully integrated with the bio-reactor (34) as a pre-sterilized package of both single-use and disposable capabilities. Items 34a and 34b, which integrate both the bio-reactor and membrane controls, are re-usable units respectively not disposable.

FIG. 4—Bio-reactor cartridge assembled from at least two envelope (40) parts (four envelopes shown), based on a semi rigid porous first matrix sheet material pre-shaped to create walls which encapsulates, and create an enclosure volume (41) for the second matrix of fibres, spheres, macro beads, grains, powders or combinations hereof.

The envelope (40) hereby appears as symmetrical core module(s) with common central fluid inlet (42) and a common outlet(s) (45b) in the circumference of the stacked core modules (40). Pore size of the envelope (40) membrane (43a, 43b) material is primarily selected to keep the fibres, spheres, macro beads, grains, powders captured by the membrane (43a, 43b) inside the envelope volume (41), but allows fluids and products to pass. The two membranes (43a, 43b) are assembled at seam 43d to circular centre part 42a with holes 42b for feed fluid to pass. The two membranes (43a, 43b) have yet a seam at the circumference 43c. For improved flow distribution, feed spacers (45a) with an array of ribs (not shown) between the envelopes (40) parts, adjacent to inlet walls (43a) ads rigidity to the envelope (40). Such spacers, or flow guides, may appear as a third matrix. The envelope (40) wall (43a, 43b) material may be of (a) symmetric structure with pore size variation suitable for the various purposes. Two or more envelopes (40) are easily assembled/stacked with inlet body seals (not shown) in between each envelope (40) centre and attached, added on top of each other, into a stack inside a suitable housing or container (not shown) creating a cartridge.

Stacked in such a way that the identical envelopes (40) create a symmetrical arrangement and the envelopes (40) share the cylindrical inlet (42) volume centre. The common inlet (42) and the common outlet (45b) are isolated from each other by the matrix material (41) inside the envelopes (40). Depending on fluid direction the cartridge centre (42) is the inlet or the outlet corresponding with the cartridge circumference (45b) is respectively the outlet or the inlet. At least two of the envelopes (40) may also be stacked inside vertical oriented capsule housing with a bottom part for at least two fluid connections and a housing dome attached with a flange and seal to the bottom part flange. The capsule may have similar design as to the capsule overall design as shown in FIG. 5.

FIG. 5—A variation of the invention is for integration purposes into a column and the bio-reactor matrix core modules is fully situated inside a stackable capsule device 50 of rigid disposable materials with at least one fluid inlet 52a and a series of symmetrical placed fluid outlets 52b integrated axially within the capsules 50 overall design. Four radial oriented and in parallel fluid outlet ports 52b are connected to drainage collection volume 53 at the capsules periphery. The bio-reactor capsule design encloses at least one set of matrix discs 51 and as here illustrated five sets of matrix discs 51. No flow spacers at the feed 52a and drainage 55b volumes between matrix discs 51 are shown for simplicity. Drainage spacers open to the collected volume 53 and closed by connection to a short tube 55d next to the inlet volume 52. Feed spacer volume 55a is not able to convey fluids to the circumference volume 53 by integrated ring 55c. The fluid is limited by entering from volume 52 directly to discs 51 at it edge by ring 55d and also restricted from exiting the discs 51 to the collection volume 53 by ring 55c. The forced fluid flow is introduced at one of two inlet 52 filling up the inlet volume 52, distributed to four full size and two half size feed spacer entrance 55a tangentially filling the feed space laminar at overpressure flowing perpendicular to the entire surface area of at least one matrix disc and through the disc for drainage spacer volume 55b further radial into circumference collection volume 53 to be conveyed to end face collection volume 56 and outlet 52b.

More than one bio-reactor capsule may be mounted on top of each other working in parallel and sealed by 50a covering both inlet 52a and exit 52b.

After the fluid has passed said fluid device the fluid may possible pass further to at least one manifold capsule, pump capsule, conditioning capsule as to the CerStack patent application (not shown). The illustrated capsule is 442 millimeters in diameter, 256 millimeter high, but may take other dimensions as required.

FIG. 6—A bio-reactor cartridge (flexible fibre sheet based pleated core) having a cylindrical shape with a longitudinal axis and a plurality of longitudinal pleats each separated by drainage spaces. The pleat material 62 may preferably be a porous material like at least one non-woven sheet of symmetrical or asymmetrical design in at least one layer. Each pleat is on both the inlet, upstream and the outlet, downstream separated by spacers 63a, 63b for flow guidance. The drainage spacers 63a, 63b may be symmetrical, identical layer(s) of at least one flow-net, screen with an array of ribs arranged coaxial allowing fluids in general and cells during feeding to pass unrestricted. Further the spacers 63a, 63b may be of asymmetrical design with coarser flow-net laminated on each side with finer mesh flow-net layers in direct contact with the porous matrix. The finer flow-net will eliminated the intrusion of fibres, particles, grains, spheres from the matrix 62 to penetrate into the spacer volume and restrict the flow passage-way. The pleated core 62 includes an upstream inlet volume for fluid distribution further include a cylindrical rigid flow-net 63c in centre 64a surrounded by the flexible pleated matrix core 62 said cylindrical centre correspond with longitudinal oriented feed spacers 63a forming semi ridged positioned in between the pleated sheet 62 in order to maintain the space between the pleats 62. The core includes on the downstream an outlet distribution volume 64b for mutual fluid collection from the individual drainage channels with spacers 63b between the pleats 62, the collection volumes 63 only receives fluids which passed the core. End caps or other means is necessary in order to passively separating the inlet for outlet (not shown). The common inlet 64a and the common outlet 64b are isolated from each other by the matrix enclosure and end caps. Depending on fluid direction the cartridge centre 64a is either the inlet or the outlet corresponding to the cartridge circumference 64b is respectively the outlet or the inlet. A variation is the encapsulation of the illustrated cartridge into a capsule, cassette with external connection, which may be easily sterilized for single-use application. Said bio-reactor cartridge comprises individual and in parallel oriented matrix walls each separated by a shared feed spacer section conveying fluids for mutually diverting of the feeding liquid to both individual matrix sections on each side of the feed spacer.

FIG. 7—A bio-reactor cartridge (flexible fibre sheet based spiral core) having a cylindrical shape with a longitudinal axis and a plurality spiral oriented layers of non-woven porous sheets 72 laminated around the drainage spacer 73b and with on each side the feed spacers 73a all wound around a central perforated fluid collection pipe 73c in the core 74. The drainage spacer 73b is shorter and less wide than the matrix sheet 72 and on three sides sealed from the feed stream with seals 72a between the matrix sheet 72, the drainage spacer 73b is connected to the collection tube 73c for fluid connection, which hereby form an envelope around the drainage spacer 73b, which is open to, connected to and in unhindered fluid correspondence with the fluid collection tube 73c. The feed spacers 73a are open on all four sides to the feed flow, and with no fluid connection to the fluid collection tube 73c except through the matrix sheets. Said cartridge comprises individual and in parallel oriented matrix sections each separated by a feed spacer section for mutually diverting feeding liquid to both individual matrix sections on each side of the feed spacer.

FIG. 8—The illustration show a body 81 with identical wall thickness all through the embodiment and two sets of opposite direction oriented conical channels 82, 83 each channel closed in only one end opposite to the inlet opening. One set of channels being the inlet channels 82 which are closed 87 in the opposite end to the fluid inlet further the drainage channels 83 of identical dimension, but of opposite arrangement. The design creates the Wall-Flow-Filter with the purpose to force fluids evenly through the walls macro porous matrix 84. The fluid flow being laminar up through the feed channels 82 and perpendicular to the porous matrix walls 84 as to the fact that the channels are conical.

FIG. 9—The illustration show an embodiment like FIG. 8 with even wall thickness, conical channel and flanged to be incorporated inside a housing (not shown) around the flange with fluid connections and flow direction from down and up. The fluid interring the matrix core 91 bottom inlet face to every feed channel 92 pass along the entire channels length, but are restricted from passing through the small end of the channel of the core 91 as the feed channel 92 is closed with blockage, plugs 97 in the end opposite of inlet face 95 conveying the fluid only along the inlet channels 92 and perpendicular through the porous wall 94 of the core 91 to the four drainage channels 93 around each feed channel 92. The figure show an axial cut through the centre of a "dead-end" honeycomb structure with the porous walls 94 arranged next to each other extending from one end to the other. A plurality of blind end channels 92, 93 extends each lengthwise from one end of the body to the other end with even wall thickness to form a wall-forced-flow body. Like a chess board every feed channel is closed in one end and every drainage channel in the other end. The core 91 is illustrated with a micro pore membrane 98 with pores finer than the macro pore matrix 91, the membrane placed on the drainage channels surface of the core for restriction purposes, inclusion, separation of desired particles and micro organism in the core matrix 91. Alternatively the feed channels are of different size and larger than the drainage channels being smaller in cross section. Design and functionality is suitable both as bio-reactor and separation devices.

FIG. 10—This embodiment is based on a rigid body 101 with non parallel walls and channels rotation symmetrical around the centre axis. Preferably cast, vacuum cast or pressed with conical feed channels 102 and conical drainage channels 103 separated by quite thick macro porous matrix walls 104 here being app 15 millimeter thick or 1.2 times thicker than the feed channel 102 inlet. The conical shape of the feed channel 102 as well as the shape of the drainage channel 103 insures laminar flow along the circular channel/even fluid speed over the channel cross section from the inlet face 105 up through every feed channel 102, which all are blocked 107 at the outlet face 106 opposite of the inlet face 105 hereby forcing an even mass flow perpendicular through the entire core 101 porous wall matrix 104 to every drainage channel 103 and to the core outlet face 106. Channel blockage 107 width is identical at both inlet face 105 and outlet face 106. The blockage end 107 wall inside width is 2.3 times smaller than the feed channel 102 inlet widths. The body may take other dimensions in order to suit specific tasks like the purpose of acting as a bio-reactor or a separation device. The illustrated embodiment measure over the flange Ø282 millimeter, 144 millimeter high, total volume (matrix+channels) of 7,400 cm$^3$, matrix volume of 4,550 cm$^3$ and the matrix is them 61% of total volume, but may take other dimensions as required.

FIG. 11—The core matrix 111 is as an alternative design to FIG. 10 illustrated with a micro porous membrane 118 with pores finer than the core 111 mounted on the outlet side of the core channel surface 113 for separation, restriction purposes like inclusion of desired particles, micro organism within the core matrix 114. Fluid passes the core 111 similar to FIG. 10. The macro porous body may take other dimensions in order to suit specific tasks like the purpose of acting as a bio-reactor or a separation device.

FIG. 12—Method—A production bio-reactor devise 121 incorporated inside a container 121a with fluid connections situated in a re-circulation fluid circuit driven continuously by at least one controlled pump. The bio-reactor 121 is operated in a perfusion system configuration with one inlet 122 and two parallel outlets 123, 124. A pump 125b controls the circuit re-circulation flow. The pump 125c controls the inlet feed of fresh nutrient and somewhat the system pressure. An air trap 126 mounted at the highest point insures bubbles are removed constantly if needed. Sensors measure the glucose, pH, temp, oxygen content, etc. and regulate the flows, valves accordingly. Further the system working pressure and the $CO^2$ content inside the reactor are measured. The oxygenator 127 insures via both way diffusion through the hollow fibre membranes the desired $O^2$ supply and $CO^2$ removal/stripping in the nutrient flow. Ratio between $O^2$ and $CO^2$ has huge influence on the pH value and the gas supplies is regulated independently and supplied to the circuit via valve 129. The pump 125c introduces the nutrient fluid to the circuit continuously from the external nutrient feed supply and at the same time the PC/PLC controls the fluid volume exiting 123 the circuit to the product vessel for external processing via the pump 125a. The pump 125b maintains the flow and circulates the perfusion volume through the reactor 121. Sensors measure the glucose and oxygen content and a PC/PLC regulate the relevant gas injection accordingly through valve 129.

FIG. 13—Method—A production bio-reactor devise 131 incorporated inside a housing 131a with fluid connections situated in a re-circulation mode with at least one fluid circuit driven continuously by at least one pump. Within this method the bio-reactor 131 housing is equipped with one reactor liquid inlet 132 and two separated reactor liquid outlets 133, 134, performing the cross-flow mode principle. The inlet flow volume through inlet tube 132 to the reactor is the combined permeate flow through outlet 133 and the retentate flow through 134. The retentate flow 134 outlet is externally re-circulated by feed pump 135b and kept preferably at constant pressure controlled by pump 135c and 135a combined. The bio-reactor 131 product flow exit 133, which is not included in the separate permeate volume flow 134, is regulated by a positive displacement pump 135a in order to obtain the desired flow over the bio-reactor matrix 131 eliminating the matrix 131 gradient by constant removal of permeate and lactate, etc. Environment regulating gases is supplied via and controlled by valve 139. Supply of dissolved oxygen is injected to the media in oxygenator 137 via external $O^2$ supply (not shown). A third pump 135c controls the inlet feed of fresh nutrient to compensate for the permeate flow losses. An air trap 136 mounted at the highest point insures potential trapped air is removed constantly. The oxygen pressure supplied to the oxygenator 137 regulates the dissolved oxygen in the nutrient feed flow.

Although some figures show cylindrical inlet volume such may be conical in order to obtain laminar flow behaviour and the circumference of the invented bio-reactor may also take other shapes as being cylindrical.

Some of the capsule, cassette examples are shown with central inlet and circumference outlet. This may be reversed according to the application. Feed and drainage may further be designed to take place in the centre and a ring area around the centre for internal capsule fluid correspondence also eliminating the circumference as drainage collection area.

While the present invention has been described in connection with particular embodiments thereof, it will be understood by those skilled in the art that many changes and modifications may be made without departing from the scope of the invention as defined by the appending claims.

The presented bio-reactor device improves the immobilization of micro organisms, in particular for anaerobic processes, such as bio technological production of therapeutic material essential or pharmacological substances.

The invention claimed is:
1. A bio-reactor for culturing immobilized living cells wherein said bio-reactor comprises a permeable disc comprising a matrix comprising a plurality of fibres defining a plurality of inter-connected, open pores extending through the disc, a bio-reactor inlet port and a bio-reactor outlet port,
wherein said matrix is suitable for anchoring living cells,
wherein said disc is in direct contact with one feeding spacer section and one drainage spacer section, respectively, on opposite sides of the disc, wherein living cells are capable of adhering to the fibres and capable of residing in at least some of the interconnected, open pores, wherein the feeding spacer section and drainage spacer section is a member selected from the group consisting of a layer of flow-nets, screens, corrugated sheets, nettings, rib stiffeners, and set of ribs or discs with a radial set of ribs, and wherein a gradient free laminar flow is created in the matrix when fluid is introduced into the bio-reactor inlet port.

2. The bio-reactor of claim 1 comprising a plurality of permeable discs that are alternately separated by feeding spacer sections and drainage spacer sections, respectively, so that each feeding spacer section provides feeding liquid to each of a first set of two adjacently located, permeable discs each drainage spacer section receives feeding fluid from each of a second set of two adjacently located permeable discs.

3. The bio-reactor according to claim 1, wherein the open pores of the matrix of the permeable discs are larger in diameter than the living cells to be cultivated, thereby allowing said cells to reside in said open pores during all or part of the duration of the cultivation.

4. The bio-reactor according to claim 1 wherein the bio-reactor is fitted with a pump in order to ensure that a desirable flow rate is obtained.

5. The bio-reactor according to claim 4, wherein the bio-reactor is further fitted with sensors and a control unit for controlling the seeding of cells and the progression of the cultivation.

6. The bio-reactor according to claim 1, wherein the thickness of the disc is less than 500 millimeters and more than 1 millimeter and wherein the diameter of the disc, including an optionally cut-out, central portion thereof, is less than 500 centimeters and more than 5 centimeters.

7. The bio-reactor according to claim 1, wherein the fibres has an average diameter in the range of from 0.01 micrometer to less than 100 micrometers.

8. The bio-reactor according to claim 1, wherein the packing density of the permeable disc fibres is in the range of from 25 to 400 kilogram/meter$^3$.

9. The bio-reactor according to claim 1, wherein the volume of the open pores of the matrix of the permeable discs is more than 40% of the volume of the disc itself.

10. The bio-reactor according to claim 1, wherein the matrix is made of non-woven fabric, woven fabric or knitted fabric.

11. The bio-reactor according to claim 1, wherein the matrix is made of fibres made of a material selected from the group consisting of ceramics, metals, cellulose or polymers such as polystyrene, polyacrylamide, polyester, nylon, polyvinyl chloride and glass, and collagen, dextran, agar, gelatine.

12. The bio-reactor according to claim 1, wherein the matrix is made of a material having an electrical charge.

13. The bio-reactor according to claim 1, wherein the reactor further comprises means for measuring operation conditions selected from means for measuring temperature, pH, glucose concentration, oxygen concentration and/or carbon dioxide concentration.

14. The bio-reactor according to claim 1, wherein the reactor further comprises means for monitoring the degree of needed replenishment of the liquid.

15. The bio-reactor according to claim 1, wherein the reactor further comprises means for regulating the temperature of the liquid.

16. The bio-reactor according to claim 1, wherein the reactor further comprises a surrounding bag.

* * * * *